United States Patent [19]

Hübsch et al.

[11] Patent Number: 4,968,681
[45] Date of Patent: Nov. 6, 1990

[54] SUBSTITUTED HYDROXYLAMINES

[75] Inventors: Walter Hübsch; Rolf Angerbauer; Peter Fey; Hilmar Bischoff, all of Wuppertal; Dieter Petzinna, Duesseldorf; Delf Schmidt, Wuppertal, all of Fed. Rep. of Germany

[73] Assignee: Bayer Aktiengesellschaft, Leverkusen, Fed. Rep. of Germany

[21] Appl. No.: 271,801

[22] Filed: Nov. 15, 1988

[30] Foreign Application Priority Data

Nov. 25, 1987 [DE] Fed. Rep. of Germany ....... 3739882

[51] Int. Cl.$^5$ .................. A61K 31/40; C07D 207/337; C07D 401/04; C07D 401/14
[52] U.S. Cl. .................... 514/248; 514/249; 514/252; 514/253; 514/256; 514/259; 514/269; 514/274; 514/307; 514/308; 514/309; 514/311; 514/312; 514/333; 514/338; 514/339; 514/341; 514/342; 514/343; 514/365; 514/367; 514/369; 514/372; 514/374; 514/375; 514/376; 514/378; 514/380; 514/387; 514/394; 514/395; 514/397; 514/414; 514/422; 514/427; 544/235; 544/237; 544/238; 544/284; 544/295; 544/296; 544/310; 544/315; 544/316; 544/333; 544/353; 544/354; 544/355; 544/356; 544/405; 546/140; 546/141; 546/142; 546/144; 546/145; 546/146; 546/147; 546/148; 546/152; 546/153; 546/155; 546/156; 546/157; 546/167; 546/170; 546/172; 546/173; 546/174; 546/176; 546/177; 546/256; 546/272; 546/273; 546/274; 546/280; 546/281; 548/152; 548/156; 548/157; 548/159; 548/170; 548/178; 548/180; 548/181; 548/182; 548/183; 548/187; 548/188; 548/189; 548/201; 548/204; 548/213; 548/214; 548/217; 548/220; 548/221; 548/224; 548/225; 548/226; 548/227; 548/228; 548/229; 548/230; 548/231; 548/232; 548/236; 548/243; 548/247; 548/248; 548/249; 548/305; 548/327; 548/328; 548/336; 548/455; 548/460; 548/461; 548/462; 548/465; 548/518; 548/519; 548/521; 548/561; 548/562; 548/523; 548/524; 548/517; 549/59; 549/60; 549/76; 549/77; 549/473; 549/494; 564/300

[58] Field of Search .......... 514/427, 248–249, 514/252–253, 256, 254, 269, 274, 307–309, 311–312, 333, 388–389, 341–342, 365–367, 369, 372, 374–376, 378, 380, 387, 394–395, 397, 414, 422; 548/561; 544/235, 237–238, 284, 295–296, 310, 315, 316, 319, 333, 353–356, 405; 546/140–142, 144–148, 152–153, 155–157, 167, 170, 172–174, 176–177, 256, 272–274, 280, 281; 548/152, 156–157, 159, 170, 178, 180–183, 187–189, 201, 204, 213–214, 217, 220, 221, 224–232, 236, 243, 247–249, 305, 327–328, 336, 455, 460–462, 465, 517–519, 521, 523, 524, 527, 562

[56] References Cited

U.S. PATENT DOCUMENTS 4,148,907 4/1979 Conti ................................ 548/561
4,231,938 11/1980 Monaghan et al. ................. 560/256
4,613,610 9/1986 Wareing .............................. 514/406

FOREIGN PATENT DOCUMENTS 0022478 1/1981 European Pat. Off. .
0114027 7/1984 European Pat. Off. .

OTHER PUBLICATIONS

Chemical Abstracts, vol. 70, No. 2, May 26, 1969, Columbus, Ohio, U.S.A. Lancini, Gian C. et al., "Synthesis of Homologs of the Antibiotic Alanosine," p. 389, Col. 1, paragraph No. 97 146h & Farmaco Ed. Sci., 1969, 24(2), 1671–3.

Chemical Abstracts, vol. 103, No. 19, 11/11/85, Columbus, Ohio, U.S.A. Han, So Yeop et al., "Synthesis of N(2)-Hydroxy-1,2,3,4,-Tetrahydro- Beta-Carbolines," p. 738, col. 1, paragraph No. 160 749z & Heterocycles 1985, 23(7), 1671–3.

Chemical Abstracts, vol. 103, No. 25, 12/23/85, Columbus Ohio, U.S.A. Strasser, Michael "N-(Naphthylalkyl-)-Hydroxylamines,", p. 866, col. 1, paragraph No. 215 016r & EP-A-O 149 588.

Primary Examiner—Mark L. Berch
Attorney, Agent, or Firm—Sprung Horn Kramer & Woods

[57] ABSTRACT

Substituted hydroxylamines of the formula

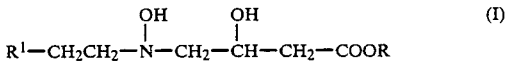

in which $R^1$ stands for an aromatic or heterocyclic radical, are especially useful in the treatment of hyperlipoproteinaemia, lipoproteinaemia and atherosclerosis.

5 Claims, No Drawings

SUBSTITUTED HYDROXYLAMINES

The invention relates to substituted hydroxylamines, intermediates for their preparation, their preparation and their use in medicaments.

It has been disclosed that lactone derivatives isolated from fungal cultures are inhibitors of 3-hydroxy-3-methyl-glutaryl coenzyme A reductase (HMG-CoA reductase) [mevinolin, EP-A 22,478; U.S. Pat. No. 231,938]. Moreover, certain indole derivatives or pyrazole derivatives are also inhibitors of HMG-CoA reductance [EP-A 1,114,027; U.S. Pat. No. 4,613,610].

Substituted hydroxylamines of the general formula

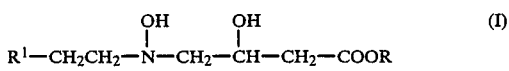

in which

R stands for hydrogen, stands for ester radical, or stands for a cation, and $R^1$ stands for a group of the formula

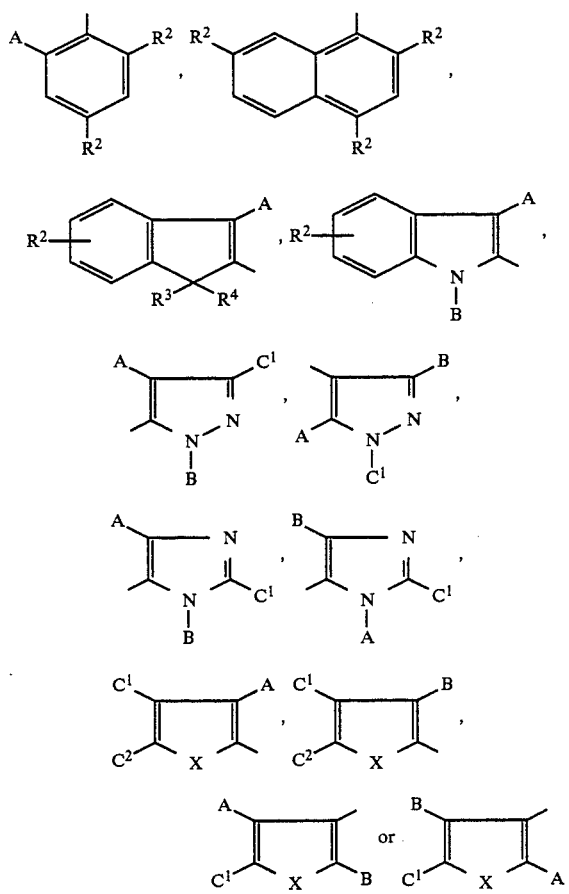

wherein $R^2$ denotes hydrogen, halogen or straight-chain or branched alkyl having up to 6 carbon atoms, $R^3$, $R^4$ are identical or different and denote hydrogen, halogen or straight-chain or branched alkyl having up to 6 carbon atoms, or $R^3$ and $R^4$ together form a tetramethylene chain, A denotes heteroaryl which can be monosubstituted, disubstituted or trisubstituted by halogen, alkyl, alkoxy, alkylthio, alkylsulphonyl, aryl, aryloxy, arylthio, arylsulphonyl, trifluoromethyl, trifluoromethoxy, trifluoromethylthio, alkoxycarbonyl or by a group of the formula —$NR^5R^6$, the substituents being identical or different, wherein $R^5$, $R^6$ are identical or different and denote alkyl, aryl, aralkyl, acyl, alkylsulphonyl or arylsulphonyl, or denotes aryl which can be monosubstituted to pentasubstituted by alkyl, alkoxy, alkylthio, alkylsulphonyl, aryl, aryloxy, arylthio, arylsulphonyl, aralkyl, aralkoxy, aralkylthio, aralkylsulphonyl, halogen, cyano, nitro, trifluoromethyl, trifluoromethoxy, trifluoromethylthio, alkoxycarbonyl, sulphamoyl, dialkylsulphamoyl, carbamoyl, dialkylcarbamoyl or by a group of the formula —$NR^5R^6$, the substituents being identical or different, wherein R5 and R6 have the abovementioned meaning, B denotes cycloalkyl, or denotes alkyl which can be substituted by halogen, cyano, alkoxy, alkylthio, alkylsulphonyl, trifluoromethyl, trifluoromethoxy, trifluoromethylthio, trifluoromethylsulphonyl, alkoxycarbonyl, acyl or by a group of the formula —$NR^5R^6$, wherein $R^5$, $R^6$ are identical or different and denote alkyl, aryl, aralkyl, acyl, alkylsulphonyl or arylsulphonyl, or by carbamoyl, dialkylcarbamoyl, sulphamoyl, dialkylsulphamoyl, heteroaryl, aryl, aryloxy, arylthio, arylsulphonyl, aralkoxy, aralkylthio or aralkylsulphonyl, where the heteroaryl and aryl radicals of the latter substituents can be monosubstituted, disubstituted or trisubstituted by identical or different halogen, cyano, trifluoromethyl, trifluoromethoxy, alkyl, alkoxy, alkylthio or alkylsulphonyl substituents, X denotes O, S or N—$C^3$, and $C^1$, $C^2$, $C^3$ are identical or different and denote hydrogen, or denote cycloalkyl, or denote alkyl which can be substituted by halogen, cyano, alkoxy, alkylthio, alkylsulphonyl, trifluoromethyl, trifluoromethoxy, trifluoromethylthio, trifluoromethylsulphonyl, alkoxycarbonyl, acyl or by a group of the formula —$NR^5R^6$, wherein $R^5$, $R^6$ have the abovementioned meaning, or by carbamoyl, dialkylcarbamoyl, sulphamoyl, dialkylsulphamoyl, heteroaryl, aryl, aryloxy, arylthio, arylsulphonyl, aralkoxy, aralkylthio or aralkylsulphonyl, where the heteroaryl and aryl radicals can be monosubstituted, disubstituted or trisubstituted by identical or different halogen, cyano, trifluoromethyl, trifluoromethoxy, alkyl, alkoxy, alkylthio or alkylsulphonyl substituents, or denotes heteroaryl which can be monosubstituted, disubstituted or trisubstituted by halogen, alkyl, alkoxy, alkylthio, alkylsulphonyl, aryl, aryloxy, arylthio, arylsulphonyl, trifluoromethyl, trifluoromethoxy, trifluoromethylthio, alkoxycarbonyl or by a group of the formula —$NR^5R^6$, the substituents being identical or different, wherein $R^5$ and $R^6$ have the abovementioned meaning, or denotes aryl which is monosubstituted to pentasubstituted by alkyl, alkoxy, alkylthio, alkylsulphonyl, aryl, aryloxy, arylthio, arylsulphonyl, aralkyl, aralkoxy, aralkylthio, aralkylsulphonyl, halogen, cyano, nitro, trifluoromethyl, trifluoromethoxy, trifluoromethylthio, alkoxycarbonyl, sulphamoyl, dialkylsulphamoyl, carbamoyl, dialkylcarbamoyl or by a group of the formula —$NR^5R^6$, the substituents being identical or different, wherein $R^5$ and $R^6$ have the abovementioned meaning, have now been found.

Surprisingly, the substituted hydroxylamines according to the invention show a superior inhibitory action on HMG-CoA reductase (3-hydroxy-3-methyl-glutaryl coenzyme A reductase).

Cycloalkyl in general stands for a cyclic hydrocarbon radical having 3 to 8 carbon atoms The cyclopropyl, cyclopentane and the cyclohexane ring Examples which may be mentioned are cyclopropyl, cyclopentyl, cyclohexyl, cycloheptyl and cyclooctyl.

Alkyl in general stands for a radical having 1 to 12 carbon atoms. Lower alkyl having 1 to about 6 carbon atoms is preferred. Examples which may be mentioned are methyl, ethyl, propyl, isopropyl, butyl, isobutyl, pentyl, isopentyl, hexyl, isohexyl, heptyl, isoheptyl, octyl and isooctyl.

Alkoxy in general stands for a straight-chain or branched hydrocarbon radical bonded via an oxygen atom and having 1 to 12 carbon atoms Lower alkoxy having 1 to about 6 carbon atoms is preferred. An alkoxy radical having 1 to 4 carbon atoms is particularly preferred. Examples which may be mentioned are methoxy, ethoxy, propoxy, isopropoxy, butoxy, isobutoxy, pentoxy, isopentoxy, hexoxy, isohexoxy, heptoxy, isoheptoxy, octoxy or isooctoxy.

Alkylthio in general stands for a straight-chain or branched hydrocarbon radical bonded via a sulphur atom and having 1 to 12 carbon atoms. Lower alkylthio having 1 to about 6 carbon atoms is preferred. An alkylthio radical having 1 to 4 carbon atoms is particularly preferred. Examples which may be mentioned are methylthio, ethylthio, propylthio, isopropylthio, butylthio, isobutylthio, pentylthio, isopentylthio, hexylthio, isohexylthio, heptylthio, isoheptylthio, octylthio or isooctylthio.

Alkylsulphonyl in general stands for a straight-chain or branched hydrocarbon radical having 1 to 12 carbon atoms which is bonded via an $SO_2$ group. Lower alkylsulphonyl having 1 to about 6 carbon atoms is preferred. Examples which may be mentioned are: methylsulphonyl, ethylsulphonyl, propylsulphonyl, isopropylsulphonyl, butylsulphonyl isobutylsulphonyl, pentylsulphonyl, isopentylsulphonyl, hexylsulphonyl and isohexylsulphonyl.

Sulphamoyl (aminosulphonyl) stands for the group $-SO_2-NH_2$.

Aryl in general stands for an aromatic radical having 6 to about 12 carbon atoms. Preferred aryl radicals are phenyl, naphthyl and biphenyl.

Aryloxy in general stands for an aromatic radical having 6 to about 12 carbon atoms which is bonded via an oxygen atom. Preferred aryloxy radicals are phenoxy or naphthyloxy.

Arylthio in general stands for an aromatic radical having 6 to about 12 carbon atoms which is bonded via a sulphur atom. Preferred arylthio radicals are phenylthio or naphthylthio.

Arylsulphonyl in general stands for an aromatic radical having 6 to about 12 carbon atoms which is bonded via an $SO_2$ group. Examples which may be mentioned are: phenylsulphonyl, naphthylsulphonyl and biphenylsulphonyl.

Aralkyl in general stands for an aryl radical having 7 to 14 carbon atoms which is bonded via an alkylene chain. Aralkyl radicals having 1 to 6 carbon atoms in the aliphatic part and 6 to 12 carbon atoms in the aromatic part are preferred. The following aralkyl radicals may be mentioned as examples: benzyl, naphthylmethyl, phenethyl and phenylpropyl.

Aralkoxy in general stands for an alkyl radical having 7 to 14 carbon atoms, where the alkylene chain is bonded via an oxygen atom. Aralkoxy radicals having 1 to 6 carbon atoms in the aliphatic part and 6 to 12 carbon atoms in the aromatic part are preferred. The following aralkoxy radicals may be mentioned as examples: benzyloxy, naphthylmethoxy, phenethoxy and phenylpropoxy.

Aralkylthio in general stands for an aralkyl radical having 7 to about 14 carbon atoms, where the alkyl chain is bonded via a sulphur atom. Aralkylthio radicals having 1 to 6 carbon atoms in the aliphatic part and 6 to 12 carbon atoms in the aromatic part are preferred. The following aralkylthio radicals may be mentioned as examples: benzylthio, naphthylmethylthio, phenethylthio and phenylpropylthio Aralkylsulphonyl in general stands for an aralkyl radical having 7 to about 14 carbon atoms, where the alkyl radical is bonded via an $SO_2$ chain. Aralkylsulphonyl radicals having 1 to 6 carbon atoms in the aliphatic part and 6 to 12 carbon atoms in the aromatic part are preferred. The following aralkylsulphonyl radicals may be mentioned as examples benzylsulphonyl, naphthylmethylsulphonyl, phenethylsulphonyl and phenylpropylsulphonyl.

Alkoxycarbonyl can be represented, for example, by the formula

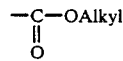

In this case, alkyl stands for a straight-chain or branched hydrocarbon radical having 1 to 12 carbon atoms. Lower alkoxycarbonyl having 1 to about 6 carbon atoms in the alkyl part is preferred. In particular, an alkoxycarbonyl having 1 to 4 carbon atoms in the alkyl part is preferred. The following alkoxycarbonyl radicals may be mentioned as examples: methoxycarbonyl, ethoxycarbonyl, propoxycarbonyl, isopropoxycarbonyl, butoxycarbonyl or isobutoxycarbonyl.

Acyl in general stands for phenyl or straight-chain or branched lower alkyl having 1 to about 6 carbon atoms, which are bonded via a carbonyl group. Phenyl and alkyl radicals having up to 4 carbon atoms are preferred. Examples which may be mentioned are: benzoyl, acetyl, ethylcarbonyl, propylcarbonyl, isopropylcarbonyl, butylcarbonyl or isobutylcarbonyl.

Halogen in general stands for fluorine, chlorine, bromine or iodine, preferably for fluorine, chlorine or bromine. Halogen particularly preferably stands for fluorine or chlorine.

Heteroaryl in general stands for a 5- to 6-membered aromatic ring which can contain oxygen, sulphur and/or nitrogen as a heteroatom and onto which can be condensed additional aromatic rings. 5- and 6-membered aromatic rings which contain one oxygen, one sulphur and/or up to 2 nitrogen atoms and which are optionally fused to benzene are preferred. Particularly preferred heteroaryl radicals which may be mentioned are: thienyl, furyl, pyrolyl, pyrazolyl, pyridyl, pyrimidyl, pyrazinyl, pyridazinyl, quinolyl, isoquinolyl, quinazolyl, quinoxalyl, phthalazinyl, cinnolyl, thiazolyl, benzothiazolyl, isothiazolyl, oxazolyl, benzoxazolyl, isoxazolyl, imidazolyl, benzimidazolyl, pyrazolyl, indolyl and isoindolyl.

If $R^1$ stands for an ester radical, then a physiologically tolerable ester radical which is easily hydrolyzed in vivo to a free carboxyl group and a corresponding physiologically tolerable alcohol is preferably meant thereby. These include, for example, alkyl esters ($C_1$ to $C_4$) and aralkyl esters ($C_7$ to $C_{10}$), preferably lower alkyl esters and benzyl esters. Moreover, the following ester radicals may be mentioned: methyl esters, ethyl esters, propyl esters and benzyl esters.

If $R^1$ stands for a cation, then a physiologically tolerable metal cation or ammonium cation is preferably meant. Alkali metal cations or alkaline earth metal cations such as, for example, cations of sodium, potassium, magnesium or calcium, and also aluminum cations or ammonium cations, and also non-toxic substituted ammonium cations from amines such as dilower alkylamines, trilower alkylamines, procaine, dibenzylamine, N,N'-dibenzylethylenediamine, N-benzyl-β-phenethylamine, N-methylmorpholine or N-ethylmorpholine, 1-ephenamine, dihydroabietylamine, N,N'-bis-dihydroabietylethylenediamine, N-lower alkylpiperidine and other amines which can be used for the formation of salts are preferred here.

Preferred compounds of the general formula (I) are those in which

R stands for hydrogen or stands for physiologically tolerable ester radical, or stands for a physiologically tolerable cation, and $R^1$ stands for a group of the formula

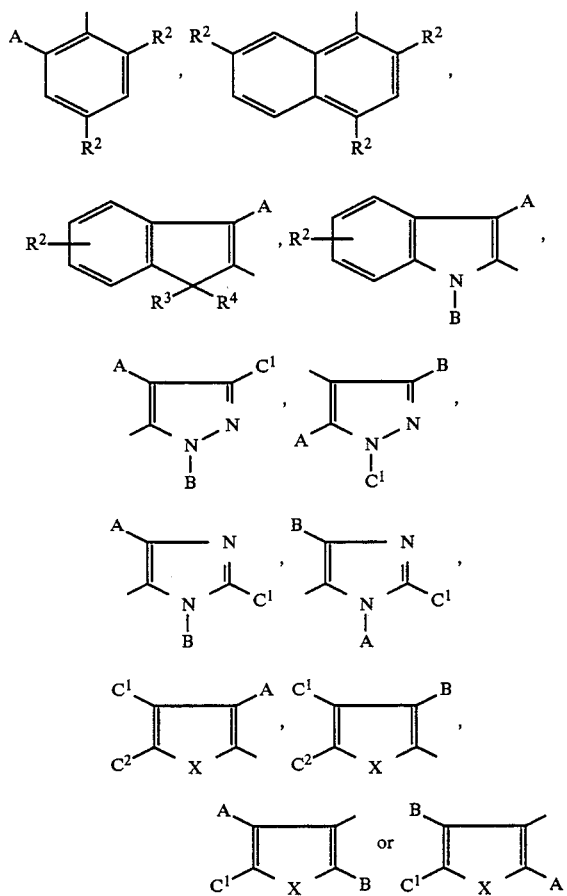

wherein $R^2$ denotes hydrogen, fluorine, chlorine, bromine, or denotes straight-chain or branched alkyl having up to 5 carbon atoms, $R^3$, $R^4$ are identical or different and denote hydrogen, fluorine, chlorine, bromine, or denote straight-chain or branched alkyl having up to 4 carbon atoms, or $R^3$ and $R^4$ together form a tetramethylene chain, A denotes thienyl, furyl, thiazolyl, isothiazolyl, oxazolyl, isoxazolyl, pyridyl, pyrimidyl, pyrazinyl, pyridazinyl, indolyl, isoindolyl, quinolyl, isoquinolyl, phthalazinyl, quinoxalinyl, quinazolinyl, cinnolinyl, benzothiazolyl, benzoxazolyl or benzimidazolyl, each of which can be monosubstituted or disubstituted by identical or different fluorine, chlorine, bromine, lower alkyl, lower alkoxy, phenyl, phenoxy, trifluoromethyl, trifluoromethoxy or lower alkoxycarbonyl substituents, or denotes phenyl or naphthyl, each of which can be monosubstituted to tetrasubstituted by lower alkyl, lower alkoxy, lower alkylthio, lower alkylsulphonyl, phenyl, phenyloxy, phenylthio, phenylsulphonyl, benzyl, benzyloxy, benzylthio, benzylsulphonyl, phenethyl, phenethoxy, phenethylthio, phenethylsulphonyl, fluorine, chlorine, bromine, cyano, trifluoromethyl, trifluoromethoxy, trifluoromethylthio, lower alkoxycarbonyl or by a group of the formula —$NR^5R^6$, the substituents being identical or different, where $R^5$ and $R^6$ are identical or different and denote lower alkyl, phenyl, benzyl, acetyl, benzoyl, phenylsulphonyl or lower alkylsulphonyl, B denotes cyclopropyl, cyclopentyl or cyclohexyl, or denotes lower alkyl which can be substituted by fluorine, chlorine, bromine, cyano, lower alkoxy, lower alkylthio, lower alkylsulphonyl, trifluoromethyl, trifluoromethoxy, trifluoromethylsulphonyl, lower alkoxycarbonyl, benzoyl, lower alkylcarbonyl, by a group of the formula —$NR^5R^6$, wherein $R^5$ and $R^6$ have the abovementioned meaning or by pyridyl, pyrimidyl, pyrazinyl, pyridazinyl, quinolyl, isoquinolyl, pyrryl, indolyl, thienyl, furyl, imidazolyl, oxazolyl, thiazolyl, phenyl, phenoxy, phenylthio, phenylsulphonyl, benzyloxy, benzylthio, benzylsulphonyl, phenethoxy, phenethylthio or phenethylsulphonyl, where the heteroaryl and aryl radicals mentioned can be monosubstituted or disubstituted by identical or different fluorine, chlorine, bromine, lower alkyl, lower alkoxy, trifluoromethyl, or trifluoromethoxy substituents, X denotes O, S or N—$C_3$, and $C_1$, $C_2$, $C_3$ are identical or different and denote hydrogen, or denote cyclopropyl, cyclopentyl or cyclohexyl, or denote lower alkyl which can be substituted by fluorine, chlorine, bromine, cyano, lower alkoxy, lower alkylthio, lower alkylsulphonyl, trifluoromethyl, trifluoromethoxy, trifluoromethylsulphonyl, lower alkoxycarbonyl, benzoyl, lower alkylcarbonyl, by a group of the formula —$NR^5R^6$, wherein $R^5$ and $R^6$ have the abovementioned meaning, or by pyridyl, pyrimidyl, pyrazinyl, pyridazinyl, quinolyl, isoquinolyl, pyrrolyl, indolyl, thienyl, furyl, imidazolyl, oxazolyl, thiazolyl, phenyl, phenoxy, phenylthio, phenylsulphonyl, benzyloxy, benzylthio, benzylsulphonyl, phenethoxy, phenethylthio or phenethylsulphonyl, where the heteroaryl and aryl radicals mentioned can be monosubstituted or disubstituted by identical or different fluorine, chlorine, bromine, lower alkyl, lower alkoxy, trifluoromethyl, or trifluoromethoxy substituents, denotes thienyl, furyl, thiazolyl, isothiazolyl, oxazolyl, isoxazolyl, pyridyl, pyrimidyl, pyrazinyl, pyridazinyl, indolyl, isoindolyl, quinolyl, isoquinolyl, phthalazinyl, quinoxalinyl, quinazolinyl, cinnolinyl, benzothiazolyl, benzoxazolyl or benzimidazolyl, each of which can be monosubstituted or disubstituted by identical or different fluorine, chlorine, bromine, lower alkyl, lower alkoxy, phenyl, phenoxy, trifluoromethyl, trifluoromethoxy or lower alkoxycarbonyl substituents, or denotes phenyl or naphthyl, each of which can be monosubstituted to tetrasubstituted by lower alkyl, lower alkoxy, lower alkylthio, lower alkylsulphonyl, phenyl, phenoxy, phenylthio, phenylsulphonyl, benzyl, benzyloxy, benzylthio, benzylsulphonyl, phenethyl, phenethoxy, phenethylthio, phenethylsulphonyl, fluorine, chlorine, bromine, cyano, trifluoromethyl, trifluoromethoxy, trifluoromethylthio, lower alkoxycarbonyl or by a group of the formula —NR$^5$R$^6$, the substituents being identical or different, where R$^5$ and R$^6$ have the abovementioned meaning.

Particularly preferred compounds of the general formula (I) are those in which

R stands for hydrogen, methyl, ethyl, propyl, isopropyl, butyl, isobutyl, tert.-butyl or benzyl, or stands for a magnesium or ammonium cation, and R$^1$ stands for a group of the formula

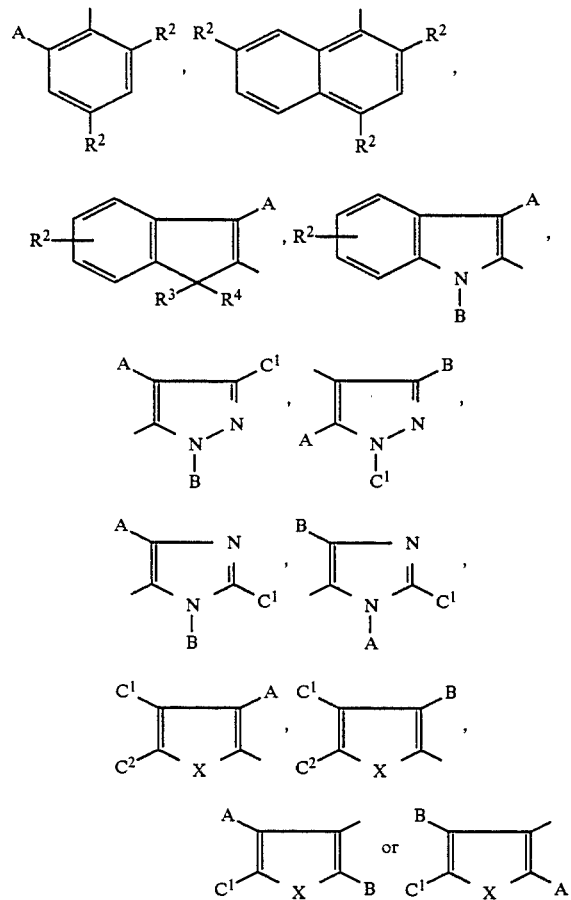

wherein

R$^2$ denotes hydrogen, fluorine, chlorine or denotes straight-chain or branched alkyl having up to 4 carbon atoms, R$^3$, R$^4$ simultaneously denote hydrogen, fluorine, chlorine or denotes alkyl having up to 3 carbon atoms, or R$^3$ and R$^4$ together form a tetramethylene chain, A denotes pyridyl, pyrimidyl, quinolyl or isorquinolyl, each of which can be substituted by fluorine, chlorine, methyl, methoxy or trifluoromethyl, or denotes phenyl which can be monosubstituted, disubstituted or trisubstituted by identical or different methyl, ethyl, propyl, isopropyl, butyl, isobutyl, tert.-butyl, methoxy, ethoxy, propoxy, isopropoxy, butoxy, isobutoxy, tert.-butoxy, methylthio, ethylthio, propylthio, isopropylthio, methylsulphonyl, ethylsulphonyl, propylsulphonyl, isopropylsulphonyl, phenyl, phenoxy, benzyl, benzyloxy, fluorine, chlorine, bromine, cyano, trifluoromethyl, trifluoromethoxy, methoxycarbonyl, ethoxycarbonyl, propoxycarbonyl, isopropoxycarbonyl, butoxycarbonyl, isobutoxycarbonyl or tert.-butoxycarbonyl substituents, B denotes cyclopropyl, cyclopentyl or cyclohexyl, or denotes methyl, ethyl, propyl, isopropyl, butyl, sec.-butyl or tert.-butyl, each of which can be substituted by fluorine, chlorine, bromine, cyano, methoxy, ethoxy, propoxy, isopropoxy, butoxy, sec.-butoxy, tert.-butoxy, methylthio, ethylthio, propylthio, isopropylthio, methylsulphonyl, ethylsulphonyl, propylsulphonyl, isopropylsulphonyl, trifluoromethyl, trifluoromethoxy, methoxycarbonyl, ethoxycarbonyl, butoxycarbonyl, isobutoxycarbonyl, tert.-butoxycarbonyl, benzoyl, acetyl, pyridyl, pyrimidyl, thienyl, furyl, phenyl, phenoxy, phenylthio, phenylsulphonyl, benzyloxy, benzylthio or benzylsulphonyl, X denotes O, S or N—C$_3$, C$_1$, C$_2$, C$_3$ are identical or different and denote hydrogen, cyclopropyl, cyclopentyl or cyclohexyl, or denote methyl, ethyl, propyl, isopropyl, butyl, isobutyl, tert.-butyl, pentyl, isopentyl, hexyl or isohexyl, each of which can be substituted by fluorine, chlorine, bromine, cyano, methoxy, ethoxy, propoxy, isopropoxy, butoxy, isobutoxy, tert.-butoxy, methylthio, ethylthio, propylthio, isopropylthio, butylthio, isobutylthio, tert.-butylthio, methylsulphonyl, ethylsulphonyl, propylsulphonyl, isopropylsulphonyl, butylsulphonyl, isobutylsulphonyl, tert.-butylsulphonyl, trifluoromethyl, trifluoromethoxy, methoxycarbonyl, ethoxycarbonyl, propoxycarbonyl, isopropoxycarbonyl, butoxycarbonyl, isobutoxycarbonyl, tert.-butoxycarbonyl, benzoyl, acetyl, ethylcarbonyl, or by a group —NR$^5$R$^6$, where R$^5$ and R$^6$ are identical or different and denote methyl, ethyl, propyl, isopropyl, butyl, isobutyl, tert.-butyl, phenyl, benzyl, acetyl, methylsulphonyl, ethylsulphonyl, propylsulphonyl, isopropylsulphonyl or phenylsulphonyl, or by pyridyl, pyrimidyl, pyrazinyl, pyridazinyl, quinolyl, isoquinolyl, thienyl, furyl, phenyl, phenoxy, phenylthio, phenylsulphonyl, benzyloxy, benzylthio or benzylsulphonyl, where the heteroaryl and aryl radicals mentioned can be substituted by fluorine, chlorine, methyl, ethyl, propyl, isopropyl, isobutyl, tert.-butyl, methoxy, ethoxy, propoxy, isopropoxy, butoxy, isobutoxy, tert.-butoxy, trifluoromethyl or trifluoromethoxy, or denotes thienyl, furyl, pyridyl, pyrimidyl, pyrazinyl, pyridazinyl, oxazolyl, isooxazolyl, imidazolyl, pyrazolyl, thiazolyl, isothiazolyl, quinolyl, isoquinolyl, benzoxazolyl, benzimidazolyl or benzthiazolyl, where the radicals mentioned can be substituted by fluorine, chlorine, methyl, ethyl, propyl, isopropyl, butyl, isobutyl, tert.-butyl, methoxy, ethoxy, propoxy, isopropoxy, butoxy, isobutoxy, tert.-butoxy, phenyl, phenoxy, trifluoromethyl, trifluoromethoxy, methoxycarbonyl, ethoxycarbonyl, isopropoxycarbonyl, propoxycarbonyl, butoxycarbonyl, isobutoxycarbonyl or tert.-butoxycarbonyl, or denotes phenyl which can be monosubstituted, disubstituted or trisubstituted by methyl, ethyl, propyl, isopropyl, butyl, isobutyl, tert.-butyl, pentyl, isopentyl, hexyl, isohexyl, methoxy, ethoxy, propoxy, isopropoxy, butoxy, isobutoxy, tert.-butoxy, methylthio, ethylthio, propylthio, isopropylthio, butylthio, isobutylthio, tert.-butylthio, methylsulphonyl, ethylsulphonyl, propylsulphonyl, isopropylsulphonyl, butylsulphonyl, isobutylsulphonyl, tert.-butylsulphonyl, phenyl, phenoxy, phenylthio, phenylsulphonyl, benzyl, benzyloxy, benzylthio, benzylsulphonyl, fluorine, chlorine, bromine, cyano, trifluoromethyl, trifluoromethoxy, trifluoromethylthio, methoxycarbonyl, ethoxycarbonyl, propoxycarbonyl, isopropoxycarbonyl, butoxycarbonyl, isobutoxycarbonyl, tert.-butoxycarbonyl or by a group —NR$^5$R$^6$, the substituents being identical or different where R$^5$ and R$^6$ have the abovementioned meaning.

Very particularly preferred compounds of the general formula (I) are those in which R stands for hydrogen, methyl or ethyl, or stands for a sodium cation or potassium cation, and R$^1$ stands for a group of the formula

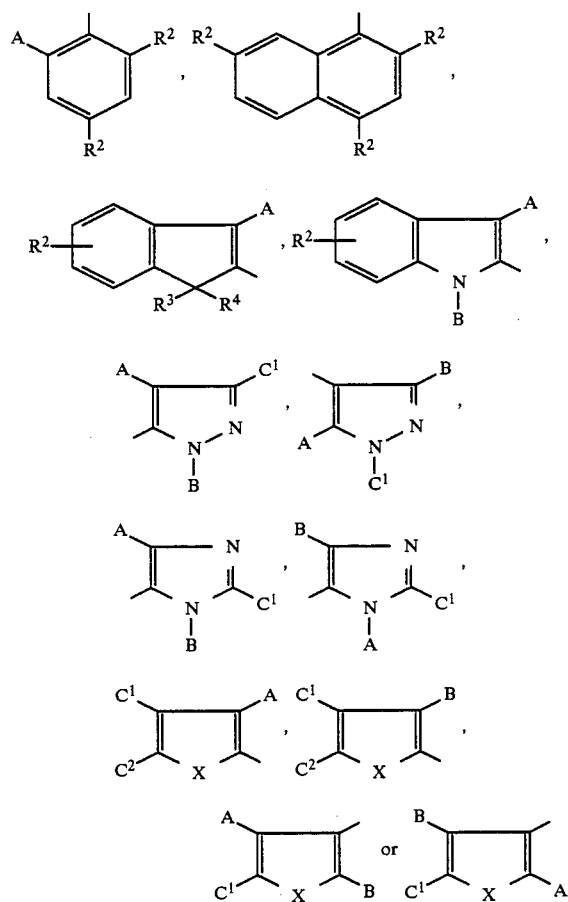

wherein

R$^2$ denotes hydrogen, flourine, chlorine or denotes straight-chain or branched alkyl having up to 4 carbon atoms, R$^3$, R$^4$ simultaneously denote hydrogen and methyl, or denote alkyl having up to 3 carbon atoms, or R$^3$ and R$^4$ together form a tetramethylene chain, A denotes phenyl which can be monosubstituted or disubstituted by identical or different methyl, ethyl, propyl, isopropyl, butyl, isobutyl, tert.-butyl, methoxy, ethoxy, propoxy, isopropoxy, phenoxy, benzyloxy, fluorine, chlorine, bromine, cyano, trifluoromethyl or trifluoromethoxy substituents, B denotes cyclopropyl, methyl, ethyl, propyl, isopropyl, butyl, isobutyl or tert.-butyl, each of which can be substituted by fluorine chlorine, methoxy, phenyl or phenoxy, X denotes O, S or N—C$^3$, C$_1$, C$_2$, C$_3$ are identical or different and denote hydrogen, cyclopropyl, cyclopentyl or cyclohexyl, or denote methyl, ethyl, propyl, isopropyl, butyl, isobutyl, tert.-butyl, pentyl, isopentyl, hexyl or isohexyl, each of which can be substituted by fluorine, chlorine, methoxy, ethoxy, propoxy, isopropoxy, methylthio, ethylthio, methylsulphonyl, ethylsulphonyl, ethoxycarbonyl, propoxycarbonyl, isopropoxycarbonyl or by a group of the formula NR$^5$R$^6$, where R$^5$ and R$^6$ are identical or different and stand for hydrogen, methyl, ethyl, propyl, isopropyl, phenyl or benzyl, or pyridyl, pyrimidyl, quinolyl, thienyl, furyl, phenyl, phenoxy, phenylsulphonyl or benzyloxy, each of which is optionally substituted by fluorine, chlorine, methyl, methoxy, trifluoromethyl or trifluoromethoxy, or thienyl, furyl, pyridyl, pyrimidyl, quinolyl, isoquinolyl, benzoxazolyl, benzthiazolyl or benzimidazolyl, each of which is optionally substituted by fluorine, chlorine, methyl, ethyl, propyl, isopropyl, methoxy, phenyl, methoxycarbonyl or ethoxycarbonyl, or denotes phenyl which is optionally monosubstituted or disubstituted by methyl, ethyl, propyl, isopropyl, butyl, isobutyl, tert.-butoxy, methoxy, ethoxy, propoxy, isopropoxy, methylthio, ethylthio, methylsulphonyl, ethylsulphonyl, phenyl, phenoxy, phenylsulphonyl, benzyloxy, fluorine, chlorine, bromine, cyano, trifluoromethyl, trifluoromethoxy, methoxycarbonyl, ethoxycarbonyl or a group of the formula —NR$^5$R$^6$, the substituents being identical or different, wherein R$^5$ and R$^6$ have the abovementioned meaning.

The substituted hydroxylamines of the general formula (I) according to the invention have at least one asymmetric carbon atom (carbon atom 3) and can therefore exist in various stereochemical forms. The invention relates both to the individual isomers and their mixtures.

The following isomeric forms of the substituted hydroxylamines may be mentioned, for example:

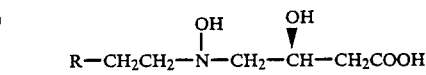

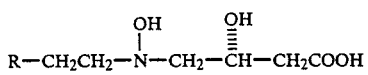

Particularly preferred compounds of the formula (I) are those in which

R stands for hydrogen, methyl or ethyl, or stands for a sodium or potassium ion, and R¹ stands for a group of the formula
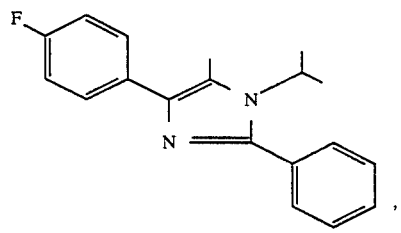,
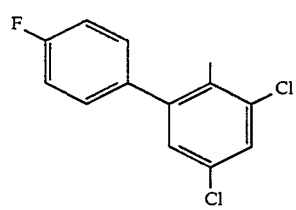,
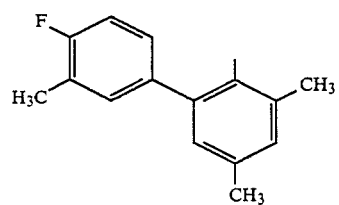,
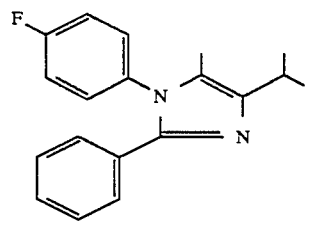,
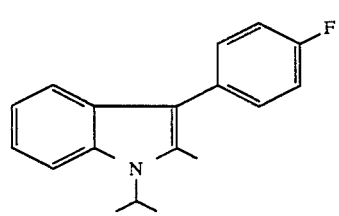,
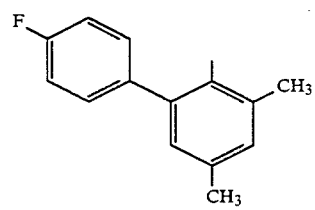,
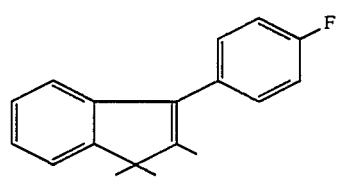,
-continued
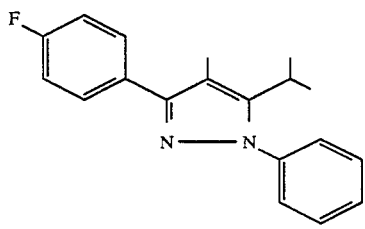,
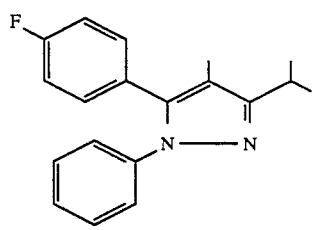,
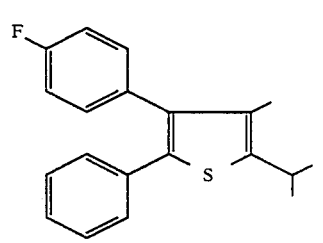,
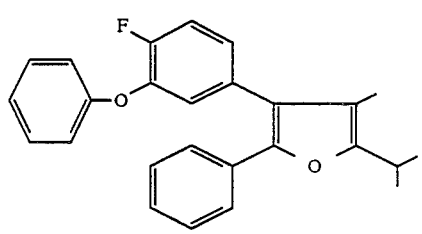,
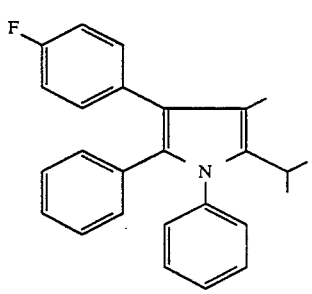,
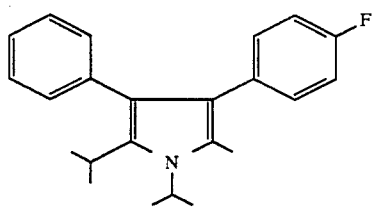, -continued

[Structure: 4-F-phenyl/phenyl/isopropyl pyrrole with N-CH2-CH3, = +]

[Structure: 4-F-phenyl/phenyl/isopropyl pyrrole with N-isopropyl]

Additionally, a process for the preparation of the substituted hydroxylamines of the general formula (I) has been found $$R^1-CH_2CH_2-\underset{|}{N}-CH_2-\underset{|}{CH}-CH_2-COOR \quad (I)$$
$$\phantom{R^1-CH_2CH_2-}OH\phantom{-CH_2-}OH$$

in which

R stands for hydrogen, stands for a physiologically tolerable ester radical, or stands for a physiologically tolerable cation, and $R^1$ stands for a group of the formula

[Structures shown: substituted phenyl, naphthyl, indene, indole, pyrazoles, imidazoles, and furan/thiophene-type rings with A, B, $C^1$, $C^2$, $R^2$, $R^3$, $R^4$, X substituents]

or [two furan/thiophene structures with A, B, $C^1$, X]

wherein $R^2$ denotes hydrogen, halogen or straight-chain or branched alkyl having up to 6 carbon atoms, $R^3$, $R^4$ are identical or different and denote hydrogen, halogen or straight-chain or branches alkyl having up to 6 carbon atoms, or $R^3$ and $R^4$ together form a tetramethylene chain, A denotes heteroaryl which can be monosubstituted, disubstituted or trisubstituted by halogen, alkyl, alkoxy, alkylthio, alkylsulphonyl, aryl, aryloxy, arylthio, arylsulphonyl, trifluoromethyl, trifluoromethoxy, trifluoromethylthio, alkoxycarbonyl or by a group of the formula —$NR^5R^6$, the substituents being identical or different, wherein $R^5$, $R^6$ are identical or different and denote alkyl, aryl, aralkyl, acyl, alkylsulphonyl or arylsulphonyl, or denotes aryl which can be monosubstituted to pentasubstituted by alkyl, alkoxy, alkylthio, alkylsulphonyl, aryl, aryloxy, arylthio, arylsulphonyl, aralkyl, aralkoxy, aralkylthio, aralkylsulphonyl, halogen, cyano, nitro, trifluoromethyl, trifluoromethoxy, trifluoromethylthio, alkoxycarbonyl, sulphamoyl, dialkylsulphamoyl, carbamoyl, dialkylcarbamoyl or by a group of the formula —$NR^5R^6$, the substituents being identical or different, wherein $R^5$ and $R^6$ have the abovementioned meaning, B denotes cycloalkyl, or denotes alkyl which can be substituted by halogen, cyano, alkoxy, alkylthio, alkylsulphonyl, trifluoromethyl, trifluoromethoxy, trifluoromethylthio, trifluoromethylsulphonyl, alkoxycarbonyl, acyl or by a group of the formula —$NR'R^6$, wherein $R^5$, $R^6$ are identical or different and denote alkyl, aryl, aralkyl, acyl, alkylsulphonyl or arylsulphonyl, or by carbamoyl, dialkylcarbamoyl, sulphamoyl, dialkylsulphamoyl, heteroaryl, aryl, aryloxy, arylthio, arylsulphonyl, aralkoxy, aralkylthio or aralkylsulphonyl, where the heteroaryl and aryl radicals of the latter substituents can be monosubstituted, disubstituted or trisubstituted by identical or different halogen, cyano, trifluoromethyl, trifluoromethoxy, alkyl, alkoxy, alkylthio or alkylsulphonyl substituents, X denotes O, S or N—$C_3$, and $C_1$, $C_2$, $C_3$ are identical or different and denote hydrogen, or denote cycloalkyl, or denote alkyl which can be substituted by halogen, cyano, alkoxy, alkylthio, alkylsulphonyl, trifluoromethyl, trifluoromethoxy, trifluoromethylthio, trifluoromethylsulphonyl, alkoxycarbonyl, acyl or by a group of the formula —$NR^5R^6$, wherein $R^5$, $R^6$ have the abovementioned meaning, or by carbamoyl, dialkylcarbamoyl, sulphamoyl, dialkylsulphamoyl, heteroaryl, aryl, aryloxy, arylthio, arylsulphonyl, aralkoxy, aralkylthio or aralkylsulphonyl, where the heteroaryl and aryl radicals of the latter substituents can be monosubstituted, disubstituted or trisubstituted by identical or different halogen, cyano, trifluoromethyl, trifluoromethoxy, alkyl, alkoxy, alkylthio or alkylsulphonyl substituents, or denotes heteroaryl which can be monosubstituted, disubstituted or trisubstituted by halogen, alkyl, alkoxy, alkylthio, alkylsulphonyl, aryl, aryloxy, arylthio, arylsulphonyl, trifluoromethyl, trifluoromethoxy, trifluoromethylthio, alkoxycarbonyl or by a group of the formula $-NR^5R^6$, these substituents being identical or different, wherein $R^5$ and $R^6$ have the abovementioned meaning, denotes aryl which is monosubstituted to pentasubstituted by alkyl, alkoxy, alkylthio, alkylsulphonyl, aryl, aryloxy, arylthio, arylsulphonyl, aralkyl, aralkoxy, aralkylthio, aralkylsulphonyl, halogen, cyano, nitro, trifluoromethyl, trifluoromethoxy, trifluoromethylthio, alkoxycarbonyl, sulphamoyl, dialkylsulphamoyl, carbamoyl, dialkylcarbamoyl or by a group of the formula $-NR^5R^6$, the substituents being identical or different, wherein $R^5$ and $R^6$ have the abovementioned meaning, which is characterized in that hydroxylamines of the general formula (II)

in which $R^1$ has the abovementioned meaning, are reacted with epoxides of the general formula (III)

in which $R^7$ stands for straight-chain or branched alkyl having up to 6 carbon atoms, in inert solvents, and then in the case of the preparation of the acids, the ester is hydrolyzed, and in the case of the preparation of the salts, the acids are reacted with the corresponding bases.

The process according to the invention can be illustrated by the following equation:

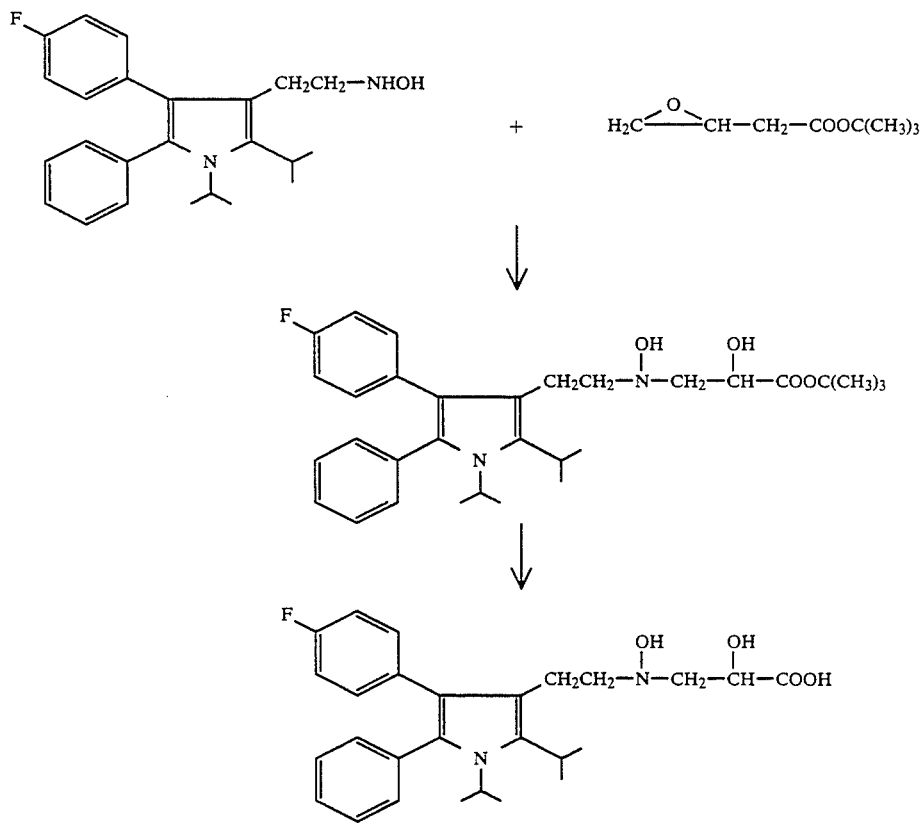

Suitable solvents in this connection are the organic solvents customary for opening an epoxide. These preferably include alcohols such as methanol, ethanol, propanol, isopropanol or butanol, or ethers such as tetrahydrofuran or dioxane, or dimethylformamide or dimethylsulphoxide. Alcohols such as methanol, ethanol, propanol or isopropanol are particularly preferably used. Likewise, it is possible to employ mixtures of the solvents mentioned.

Moreover, it is also possible to employ auxiliaries such as titanium (IV) isopropoxide or boron trifluoride etherate in aprotic solvents such s, for example, chlorinated hydrocarbons, preferably methylene chloride or aromatic hydrocarbons such as toluene, xylene or benzene.

The reaction is in general carried out in a temperature range from 0° C. to +150° C., preferably from +20° C. to +100° C.

In general, the reaction is carried out at normal pressure. However, it is also possible to work at reduced pressure or elevated pressure (for example from 0.5 to 5 bar).

For carrying out the process according to the invention, the epoxide is in general employed in an amount from 0.5 to 2 moles. Preferably, molar amounts of reactants are used.

For the preparation of the carboxylic acids according to the invention (R=H), the carboxylates are in general hydrolyzed by customary methods. The hydrolysis in general takes place by treating the ester in inert solvents with customary acids, where in general the salts of the compounds according to the invention result first, which can then be converted into the free compounds in a second step by treating with base.

The customary mineral acids, and also carboxylic acids or sulphonic acids, can be employed as acids. These preferably include inorganic acids such as, for example, hydrochloric acid or sulphuric acid, or organic carboxylic acids having 1 to 6 C atoms, if appropriate substituted by fluorine, chlorine and/or bromine, such as, for example, acetic acid, trifluoroacetic acid, trichloroacetic acid or propionic acid, or sulphonic acids having $C_1$-$C_4$-alkyl radicals or having aryl radicals such as, for example, methanesulphonic acid, ethanesulphonic acid, benzenesulphonic acid or toluenesulphonic acid. The hydrolysis is particularly preferably carried out using hydrochloric acid.

For the hydrolysis, water or the organic solvents customary for hydrolysis are suitable. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. Likewise, it is possible to employ mixtures of the solvents mentioned.

The hydrolysis of the tertiary butyl ester is particularly preferably carried out in aqueous hydrochloric acid, if appropriate with the addition of a solvent such as, for example, dioxane or tetrahydrofuran, or using gaseous hydrogen chloride in halogenated hydrocarbons such as methylene chloride or chloroform.

The hydrolysis is in general carried out in a temperature range from 0° C. to +100° C., preferably from +20° C. to +80° C.

In general, the hydrolysis is carried out at normal pressure. However, it is also possible to work at reduced pressure or elevated pressure (for example from 0.5 to 5 bar).

The epoxides of the general formula (III) employed as starting materials are known [J. Muggel and O. Vogl, J. Polym. Sci. Polym. Chem. Ed. 22, 2501–21 (1984); S. Boots and M. R. Boots, J. Pharm. Sci. 64, 1262-1264 (1975)]and can be prepared, for example, by reaction of but-3-enoic acid esters with peracids.

Examples of epoxides which may be mentioned are: tert.-butyl 3,4-epoxybutyrate, methyl 3,4-epoxybutyrate, ethyl 3,4-epoxybutyrate, propyl 3,4-epoxybutyrate, isopropyl 3,4-epoxybutyrate, isobutyl 3,4-epoxybutyrate and n-butyl 3,4-epoxybutyrate.

The hydroxylamines of the formula (II) employed as starting materials are new.

A process for the preparation of the hydroxylamines of the general formula (II)

$$R^1—CH_2CH_2—NH—OH \qquad (II)$$

in which $R^1$ stands for hydrogen, stands for a physiologically tolerable ester radical, or stands for a physiologically tolerable cation, has been found, which is characterized in that in a first step, aldehydes of the general formula (IV)

$$R—CHO \qquad (IV)$$

in which

R has the abovementioned meaning are reacted with nitromethane in inert solvents, if appropriate in the presence of auxiliaries, and subsequently in a second step, the nitro compounds obtained of the general formula (V)

$$R—CH=CH—NO_2 \qquad (V)$$

are reduced in inert solvents, if appropriate in the presence of an auxiliary.

The process according to the invention can be illustrated by the following equation:

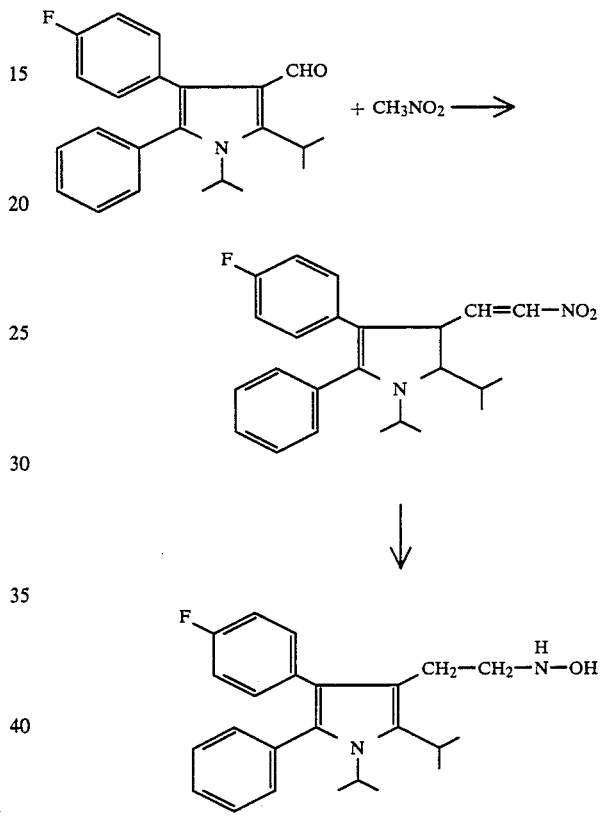

For the first step, the customary organic solvents which are not altered by the reaction conditions are suitable as solvents. These preferably include water or alcohols such as methanol, ethanol, propanol or isopropanol, or ethers such as diethyl ether, butyl methyl ether, dioxane, tetrahydrofuran or glycol dimethyl ether, or halogenated hydrocarbons such as, for example, methylene chloride, chloroform or carbon tetrachloride, or hydrocarbons such as benzene, toluene, xylene or mineral fractions, or amides such as dimethylformamide or hexamethylphosphoric triamide, or dimethyl sulphoxide, acetic acid, trifluoroacetic acid or nitroalkanes. Likewise, it is possible to use mixtures of the solvents mentioned.

Acids or bases are suitable as auxiliaries. Alkali metal hydroxides or alkaline earth metal hydroxides such as sodium hydroxide, potassium hydroxide or barium hydroxide, or alkali metal carbonates such as sodium carbonate or potassium carbonate, or alkali metal alkoxides such as sodium methoxide, sodium ethoxide, potassium methoxide, potassium ethoxide, potassium tert.-butoxide or ammonia, or ammonium acetate, or organic amines such as diethylamine, triethylamine, diisopropylamine, tripropylamine, pyridine, piperidine, morpholine, N,N-dimethylaminopyridine, DBN, DBU, ethylenediamine or N,N-dimethylethylenediamine are preferably employed as bases.

Inorganic acids such as, for example, hydrochloric acid or sulphuric acid or organic carboxylic acids having 1–6 carbon atoms, if appropriate substituted by fluorine or chlorine, such as, for example, formic acid, acetic acid, propionic acid, chloroacetic acid, trichloroacetic acid or trifluoroacetic acid, or sulphonic acids, such as, for example, methanesulphonic acid, ethanesulphonic acid, benzenesulphonic acid or toluenesulphonic acid are preferably employed as acids.

It has proved particularly favorable to carry out the first step of the process in acetic acid as the solvent, if appropriate in the presence of piperidine or ammonium acetate, or in nitromethane as the solvent and ethylenediamine as the catalyst.

The first step of the process is in general carried out in a temperature range from 0° C. to 150° C., preferably from +20° C. to +100° C.

The reaction can be carried out at normal, elevated or reduced pressure (for example 0.5 to 5 bar). In general, the reaction is carried out at normal pressure.

For carrying out the first step of the process, in general nitromethane is employed in an amount from 0.1 to 100, preferably from 0.5 to 100, particularly preferably from 1 to 60 moles relative to 1 mole of the aldehyde.

The process step according to the invention is in general carried out by mixing the aldehyde with nitromethane, if appropriate in a suitable solvent and if appropriate using bases, and if appropriate warming. Working up takes place in a customary manner by extraction, chromatography and/or crystallization.

The reduction in the second step of the reaction is in general carried out in inert solvents using $BH_3$ as the reductant, if appropriate in the presence of other hydrides as catalysts.

Ethers such as diethyl ether, dioxane or preferably tetrahydrofuran, or hydrocarbons such as benzene, toluene, xylene, hexane or cyclohexane are suitable as inert solvents here.

Metal hydrides, such as, for example, sodium borohydride, lithium borohydride or sodium cyanoborohydride inter alia are suitable as catalysts.

The reduction can be carried out particularly well using $BH_3$ in tetrahydrofuran in the presence of a catalytic amount of sodium borohydride.

The reduction in general takes place in a temperature range from −78° C. to +40°, preferably from −20° C. to room temperature.

The process according to the invent on is in general carried out at normal pressure. However, it is also possible to carry out the process at reduced pressure or elevated pressure (for example in a range from 0.5 to 5 bar).

In general, the reductant is employed in an amount of 1 to 5 moles, preferably from 1 to 2 moles, relative to 1 mole of the keto compound.

The aldehydes employed as starting materials are known or can be prepared by known methods [G. E. Stokker et al., J. Med. Chem. 29, 170, (1986); EP 221,025; U.S. Pat. No. 4,668,794; U.S. Pat. No. 4,613,610; EP 114,027].

Aldehydes which can be used according to the invention, for example, are: 4'-fluoro-3,3',5-trimethyl-1,1'-5-phenyl-2-carboxaldehyde, 4'-fluoro-3,5-dimethyl-1,1'-biphenyl-2-carboxaldehyde, 3,5-dichloro-4'-fluoro-1,1'-bi-phenyl-2-carboxaldehyde, 3-(4'-fluorophenyl)-1-isopropyl-indole-2-carboxaldehyde, 3-(4'-fluorophenyl)-1H-indene-2-carboxaldehyde, 3-(4'-fluorophenyl)-3-isopropyl-1-phenyl-1H-pyrazole-4-carboxaldehyde, 5-(4'-fluorophenyl)-3-isopropyl-1-phenyl-1H-pyrazole-4-carboxaldehyde, 4-(4'-fluorophenyl)-1-isopropyl-2-phenyl-1H-imidazole-5-carboxaldehyde, 1-(4'-fluorophenyl)-4-isopropyl-2-phenyl-1H-imidazole-5-carboxaldehyde, 3-(4-fluorophenyl)-5-isopropyl-1-methyl-2-phenyl-pyrrole-4-carboxaldehyde, 2-formyl-1-(4fluorophenyl)-3-isopropyl-5-phenylpyrrole, 2-formyl-3-(4-fluorophenyl)-1-isopropyl-5-phenylpyrrole, 2-formyl-3-(4-fluorophenyl)-1,5-diisopropyl-4-phenylpyrrole, 3-formyl-4-(4-fluorophenyl)-2-isopropyl-5-phenylfuran, 3-formyl-4-(4-fluorophenyl)-2-isopropyl-5-phenylthiophene, 2-tert.-butyl-3-formyl-4-(4-fluorophenyl)-5-phenylfuran, 3-formyl-4-(4-fluorophenyl)-2,5-diphenylthiophene, 3-formyl-2-(4-fluorophenyl)-5-methyl-1-phenyl-4-isopropylpyrrole, 3-formyl-2-(4-fluorophenyl)-5-methyl-1-(2,6-dimethylphenyl)-4-isopropylpyrrole, 3-formyl-2-(4-fluorophenyl)-1-benzyl-4-isopropyl-5-methylpyrrole, 4-(4-chlorophenyl)-3-formyl-2-isopropyl-1-methyl-5-phenylpyrrole, 3-formyl-4-(4-fluorole-3-phenoxyphenyl)-2-isopropyl-1,5-dimethylpyrrole, 3-formyl-4-(4-fluoro-3-phenoxyphenyl)-2-isopropyl-5-phenylpyrrole, 3-formyl-4,5-bis-(4-fluorophenyl)-2-isopropyl-1-methylpyrrole, 3-[3-(4-fluorobenzyloxy)]phenyl-3-formyl-2-isopropyl-1-methyl-4-phenyl, 4-(4-fluorophenyl)-3-formyl-2-isopropyl-5-phenylpyrrole, 4-(4-fluorophenyl)-3-formyl-1,2-diisopropyl-5-phenylpyrrole, 4-(4-fluorophenyl)-3-formyl-2-isopropyl-1,5-diphenylpyrrole, 4-(4-fluorophenyl)-3-formyl-2-isopropyl-1-(4-methoxyphenyl)-5phenylpyrrole, 1-(3-benzylphenyl)-4-(4-fluorophenyl)-3-formyl-2-isopropyl-5-methylpyrrole.

The substituted hydroxylamines according to the invention can be used in medicaments for the therapeutic treatment of humans and animals. Preferably, they can be used as inhibitors of 3-hydroxy-3-methyl-glutaryl coenzyme A (HGM-CoA) reductase and inhibitors of cholesterol biosynthesis. They can therefore be used for the treatment of hyperlipoproteinaemia, lipoproteinaemia or atherosclerosis.

The new active compounds may be converted in a known manner into the customary formulations such as tablets, dragees, pills, granules, aerosols, syrups, emulsions, suspensions and solutions, using inert, non-toxic, pharmaceutically suitable excipients or solvents. In this case, the therapeutically active compound should in each case be present in a concentration from about 0.5to 98% by weight, preferably 1 to 90% by weight, of the total mixture, i.e. in amounts which are sufficient to achieve the given dosage range.

The formulations are prepared, for example, by extending the active compounds with solvents and/or excipients, if appropriate using emulsifiers and/or dispersants, where, for example, in the case of the use of water as a diluent, organic solvents can be used, if appropriate, as auxiliary solvents.

Auxiliaries which may be mentioned, for example, are: water, non-toxic organic solvents, such as paraffins (for example mineral oil fractions), vegetable oils (for example groundnut/sesame oil), alcohols (for example: ethyl alcohol, glycerol), excipients, such as, for example, ground natural minerals, for example kaolins, aluminas, talc, chalk), ground synthetic minerals (for example highly disperse silica, silicates), sugars (for example sucrose, lactose and dextrose), emulsifiers (for example polyoxyethylene fatty acid esters, polyoxyethylene fatty alcohol ethers, alkylsulphonates and arylsulphonates), dispersants (for example lignin-sulphite waste liquors, methylcellulose, starch and polyvinylpyrrolidone) and lubricants (for example magnesium stearates, talc, stearic acid and sodium lauryl sulphate).

The administration takes place in a customary manner, preferably orally, parenterally, perlingually or intravenously. In the case of oral use, tablets may of course also contain additives, such as sodium citrate, calcium carbonate and dicalcium phosphate together with various additives, such as starch, preferably potato starch, gelatin and the like in addition to the excipients mentioned. Furthermore, lubricants, such as magnesium stearate, sodium lauryl sulphate and talc can additionally be used for tabletting. In the case of aqueous suspensions, the active compounds may be used with various flavour-improvers or colorants in addition to the abovementioned auxiliaries.

For the case of parenteral use, solutions of the active compound using suitable liquid excipients may be employed.

In general, it has proved advantageous with intravenous administration to administer amounts from about 0.001 to 1 mg/kg, preferably about 0.01 to 0.5 mg/kg of body weight to attain effective results, and with oral administration the dosage is about 0.1 to 20 mg/kg, preferably 0.1 to 10 mg/kg of body weight.

In spite of this, it may be necessary to deviate from the amounts mentioned, depending on the body weight or the type of application routes, on individual behaviour towards the medicament, the type of its formulation and the time or interval at which administration takes place. Thus, in some cases it may be sufficient to manage with less than the previously mentioned minimum amount, whereas in other cases the upper limit mentioned must be exceeded. In the case of the administration of larger amounts, it can be advisable to divide these into several individual doses over the day.

PREPARATION EXAMPLES

Example 1

1-(4-Fluorophenyl)-4-methylpent-1-en-3-one

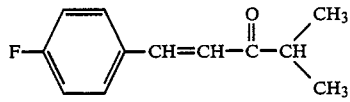

75 ml of 15% strength potassium hydroxide solution are added dropwise to 198.4 g (1.6 mol) of freshly distilled 4-fluorobenzaldehyde and 137.6 g (1.6 mol) of methyl isopropyl ketone in 300 ml of methanol and stirred overnight at room temperature. The mixture is then neutralized using 10 ml of acetic acid, 1 l of water is added and the mixture is extracted with two 500 ml portions of ether. The combined organic phases are washed with 500 ml of saturated sodium chloride solution and dried over sodium sulphate. After removing the solvent, the residue is distilled under high vacuum.

Yield: 198.6 g (65% of theory) of yellowish oil.

B.p.: 103° C. (0.3 mbar).

$^1$H-NMR (CDCl$_3$): δ=1.2 (d, 6H, CH$_3$); 2.9 (septet, 1H, CH-(CH$_3$)$_2$); 6.8 (d, 1H, olefinic-H); 7.1 (m, 2H, aromatic-H); 7.6 (m, 3H, aromatic-H+olefinic-H).

Example 2

2-(4-Fluorophenyl)-5-methyl-1-phenylhexane-1,4-dione

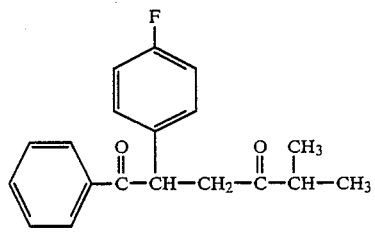

A solution of 110 g (1.04 mol) of freshly distilled benzaldehyde in 500 ml of dimethylformamide are added dropwise at 35° C. to 10.2 g (0.21 mol) of sodium cyanide in 500 ml of dimethylformamide in the course of 30 minutes and stirred for a further 5 minutes at this temperature. 150 g (0.78 mol) of 1-(4-fluorophenyl)-4-methyl-pent-1-en-3-one (Example 1) in 500 ml of dimethylformamide are then added in the course of 1.5 hours and the mixture is stirred for 1 more hour, the temperature being kept constant at 35° C.

After adding 1.5 l of water, the mixture is extracted four times using 500 ml of chloroform each time, and the combined organic phases are washed with 800 ml of 0.01 M H$_2$SO$_4$, 800 ml of saturated sodium hydrogen carbonate solution and 1.5 l of water and dried over magnesium sulphate. After removing the solvent, the residue is distilled under high vacuum.

Yield: 167 g (72% of theory) of colorless oil.

b.p.: 165° C. (0.1 mbar), which slowly crystallizes.

m.p.: 54–55° C.

$^1$H-NMR (CDCl$_3$): δ=1.08 (d, 3H, CH$_3$); 1.12 (d, 3H, CH$_3$); 2.65 (septet, 1H, CH—(CH$_3$)$_2$); 2.7 (dd, 1H, —CO—CH$_2$—CH); 3.6 (dd, 1H, —CO—CH$_2$—CH); 5.12 (dd, 1H, H—C—C$_6$H$_4$—F); 6.95 (m, 2H, aromatic-H); 7.23 (m, 2H, aromatic-H); 7.4 (m, 3H, aromatic-H); 7.95 (m, 2H, aromatic-H).

Example 3

3-(4-Fluorophenyl)-1,5-diisoprooyl-2-phenylpyrrole

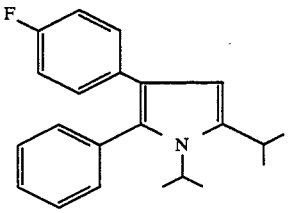

A solution of 56 g (0.29 mol) of titanium tetrachloride in 200 ml of toluene is added dropwise at 10° C. to 80 g (0.27 mol) of Example 2 and 96 g (1.63 mol) of isopropylamine in 300 ml of toluene, and stirred for 5 hours at RT. The mixture is filtered over kieselguhr, washed with hot toluene and the organic phases are extracted using water, 1N hydrochloric acid and saturated sodium hydrogen carbonate solution. After removing the toluene, a residue remains which is crystallized from petroleum ether.

Yield: 51 g of colorless crystals.

m.p.: 147° C.

Example 4

3-(4-Fluorophenyl)-4-formyl-1,5-diisopropyl-2-phenylpyrrole

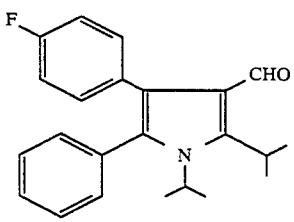

11 g (0.12 mol of phosphorus oxychloride are added dropwise with care to a suspension of 38.6 g (0.12 mol) of the compound of example 3 in 140 g (1.92 mol) of dimethyl formamide; the mixture is stirred for 1 h at room temperature and then for 30 mins. at 60° C until all the components have dissolved.

The solution is poured on to 1 l of cold 0.1N sodium hydroxide
solution, a further 150 ml of 1N sodium hydroxide solution are added and the mixture is stirred for 15 mins. at room temperature (pH 7). It is extracted four times, each time with 250 ml of dichloromethane and the organic phases are washed with 300 ml each of saturated sodium hydrocarbonate solution and water and dried over sodium sulphate.

The product is evaporated to form a crystal slurry which yields 35 g (85%) of yellowish crystals when crystallized several times from ethanol.

M.p. = 197° C.

Example 5

1-/3-(4-Fluorophenyl)-1,5-diisopropyl-2-phenylpyrrol-4-yl/-2-nitroethene

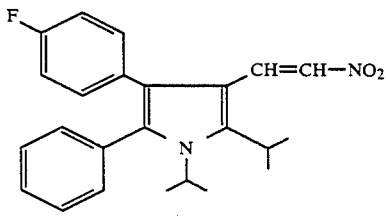

18.1 g (51.8 mmol) of the compound of example 4 are stirred in 140 g of nitromethane with 0.53 g (8.83 mmol) of 1,2-diaminoethane for 1.5 h at 75° C. After cooling, the product is filtered off and washed with petroleum ether.

Yield: 19.8 g (97% of theory) of yellow crystals.

m.p. 256° C. (crystallized from dichloromethane and petroleum ether).

¹H-NMR (CDCl₃):δ=(d, 6 H, C-isopropyl-CH₃); 1.6 (d, 6 H, N-isopropyl-CH₃); 3.6 (septet, 1 H, C-isopropyl-H); 4.9 (septet, 1 H, N-isopropyl-H); 6.5 (d, 1 H, olefinic-H); 6.8–7.3 (m, 9 H, aromatic-H); 8.4 (d, 1 H, olefinic-H).

Example 6

N-{2-[3-(4-Fluorophenyl)-1,5-diisopropyl-2-phenylpyrrol-4-yl]ethyl}hydroxylamine

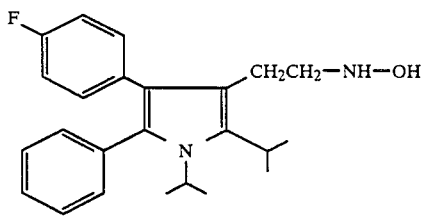

A solution of 30 g (76.5 mmol) of the compound of example 5 in 200 ml of warm tetrahydrofuran is added dropwise to 19.1 ml (0.19 mol) of a 1N solution of borane acid in tetrahydrofuran at 0° C. under an argon atmosphere; 0.5 g (13.2 mmol) of sodium hydridoborate are then added and the mixture is stirred for 2 h at room temperature. Then 180 ml of cold water are added dropwise with care and the mixture is boiled for 1 h under reflux. The mixture is adjusted to a pH of 13 with 10 ml of 6N sodium hydroxide solution, extracted three times, each time with 200 ml of ethyl acetate and the combined organic phases are dried over sodium sulphate and evaporated to dryness. The residue is chromatographed on 500 g of silica gel (230 to 400 mesh) with dichloromethane, dichloromethane/methanol (10:1) and dichloromethane/methanol/concentrated ammonia (100:10:1) until the main product emerges with the lowest Rf-value.

Yield: 13.5 g (46% of theory) of colourless crystals of a melting point of 182° C. (crystallized from dichloromethane/methanol).

¹H-NMR (CDCl₃): δ = 1.4 (m, 12 H, isopropyl-CH₃); 2.7–(m, 4 H, CH₂); 3.4 (septet, 1 H, C-isopropyl-H); 4.45 (m, 1 H, N-isopropyl-H) 4,9 (b, 2 H; 6.8–7.3 (m, 9 H, aromatic-H).

Example 7

N-{2-[3-(4-Fluorophenyl)-1,5-diisopropyl-2-phenylpyrrol-4-yl]ethyl}-N-(3-tertiary butoxycarbonyl-2-hydroxypropyl) hydroxylamine

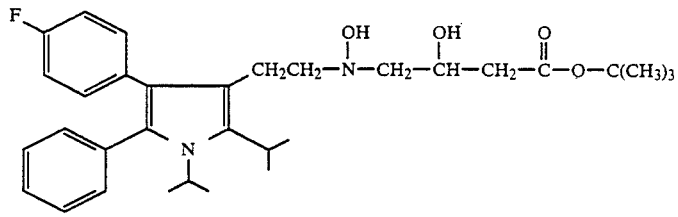

0.9 g (2.37 mol) of Example 6 are heated at reflux for 24 hours with 0.37 g (2.37 mmol) of tertiary butyl 3,4-epoxybutyrate in 30 ml of absolute ethanol. After removing the solvent, the residue is chromatographed on 50 g of silica gel 230–400 mesh in a column of 1.5 cm diameter using petroleum ether/ethyl acetate 5:1. 0.9 g of colorless less foam is obtained.

¹H-NMR (CDCl₃)δ=1.45 (s, 9 H, t-butyl); 2.3 (d, 2 H, CH₂-COOR); 2.45–2.65 (m, 4 H, CH₂); 2.9 (m, 2 H, CH₂); 3.4 (m, b, 2 H, C-isopropyl-H and OH); 4.15 (m, 1 H, H-C-OH); 4.45 (septet, 1 H, N-isopropyl-H); 4.95 (b, 1 H, OH); 6.8–7.25 (m, 9 H, aromatic-H).

Example 8

N-{2-[3-(4-Fluorophenyl)-1,5-diisopropyl-2-phenylpyrrol-4-yl]ethyl}-N-(3-carboxy-2-hydroxypropyl)hydroxylamine hydrochloride

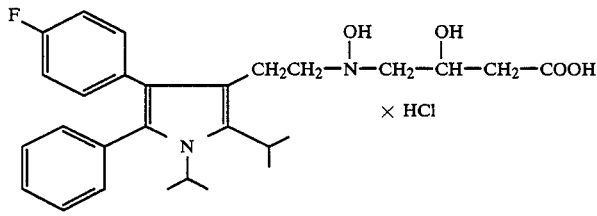

1.25 g (2.32 mmol) of Example 7 are heated at reflux for 3 hours in 70 ml of 1N hydrochloric acid. After concentrating, the residue is dried over phosphorus pentoxide.

Yield: 1.17 g (98%) of slightly colored foam.
R_f: 0.4 (chloroform/methanol (2:1) on silica gel)
¹H-NMR (CDCl₃): ε=1.4 (m, 12 H, isopropyl-CH₃); 2.35 (m, 2 H, CH₂); 2.8–3.2 (m, 6 H, CH₂); 3.4 (m, 1 H, C-isopropyl-H); 4.45 (m, 1 H, N-isopropyl-H); 3.9–5.2 (b, OH, NH, (HO)-CH).

Example 9

1-Ethyl-3-(4-fluorophenyl)-5-isopropyl-2-phenylpyrrole

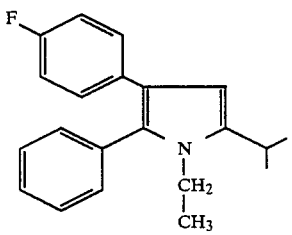

Sufficient ethanol is added to a boiling mixture of 8.2 g (27.5 mmol) of Example 2 in 25 ml of 50% strength aqueous ethylamine that a clear solution results and the mixture is heated at reflux for 1 hour. The ethanol is removed, the residue is partitioned between water and chloroform, and the organic phase is washed with saturated sodium chloride solution and dried over sodium sulphate. After concentrating to dryness, 4.5 g (53%) of colorless crystals are obtained of m.p.: 110° C. ¹H-NMR (CDCl₃): δ=1.1 (t, 3 H, CH₃); 1.35 (d, 6 H, isopropyl-CH₃); 3.0 (septet, 1 H, isopropyl-H); 3.85 (q, 2 H, CH₂); 6.15 (s, 1 H, 4-H); 6.7–7.4 (m, 9 H, aromatic-H).

Example 10

N-{2-[1-Ethyl-3-(4-fluorophenyl)-5-isopropyl-2-phenylpyrrol-4-yl]ethyl}-N-(3-tertiary butoxycarbonyl-2-hydroxypropyl)hydroxylamine

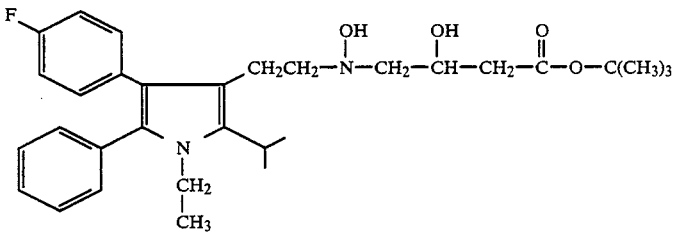

The compound is obtained from the compound from Example 9 in analogy to the Examples 4–7. Colorless foam.

¹H-NMR (CDCl₃): ε=1.1 (t, 3 H, CH₂-CH₃); 1.45 (m, 15 H, isopropyl-CH₃ and tertiary butyl-CH₃); 2.35 (d, 2 H, CH₂-COOR); 2.55–2.9 (m, 6 H, CH₂); 3.2 (m, 1 H, isopropyl-H); 3.9 (q, 2 H, CH₂-CH₃); 4.15 (m, 1 H, (HO)-CH); 6.8–7.3 (m, 9 H, aromatic-H).

Example 11

N-{2-[1-Ethyl-3-(4-fluorophenyl)-5-isopropyl-2-phenylpyrrol-4-yl]-ethyl}-N-(3-carboxy-2-hydroxypropyl)hydroxylamine hydrochloride

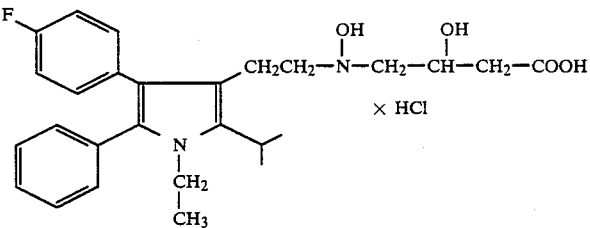

The compound is obtained from the compound from Example 10 analogously to Example 8.

Colorless foam
R$_f$=0.2 (chloroform/methanol 5:1).

Example 12

3-(4-Fluorophenyl)-5-isopropyl-1,2-diphenylpyrrole

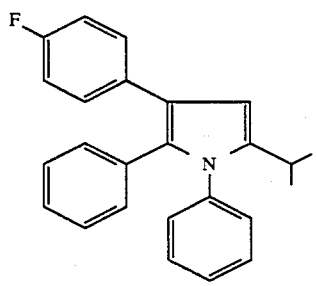

10.1 g (34 mmol) of 2-(4-fluorophenyl)-5-methyl-1-phenylhexane-1,4-dione (Example 2) and 9.3 g (102 mmol) of aniline are heated under reflux for 24 hours in a water separator in 150 ml of toluene with the addition of 500 mg of p-toluenesulphonic acid. After cooling and diluting with ethyl acetate, the mixture is washed with 1N hydrochloric acid and then with sodium hydrogen carbonate solution, dried over magnesium sulphate and concentrated in vacuo. The residue is then chromatographed over silica gel.

Yield: 4.4 g (37% of theory)

$^1$H-NMR (CDCl$_3$): δ=1.17 (d, 6 H); 2.70 (septet, 1 H); 6.28 (s, 1 H); 6.80–7.30 (m, 14 H).

Example 13

N-{2-[3-(4-Fluorophenyl)-5-isopropyl-1,2-diphenylpyrrol-4-yl]ethyl}-N-(3-tertiary butoxycarbonyl-2-hydroxypropyl)hydroxylamine

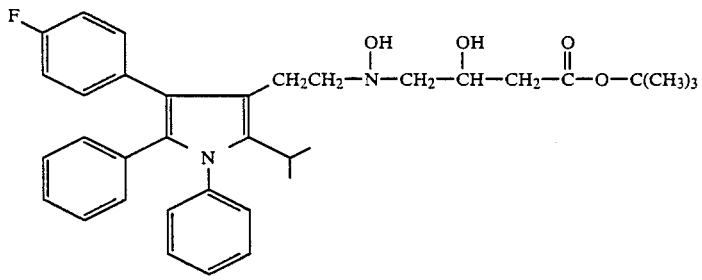

The compound is obtained from the compound of Example 12 analogously to Example 4–7. Colorless foam.

$^1$H-NMR (CDCl$_3$): ε=1.25 (d, 6 H, isopropyl-CH$_3$); 1.45 (s, 9 H, t-but.-CH$_3$); 2.4 (d, 2 H, CH$_2$-COOR); 2.5–2.75 (m, 4 H, CH$_2$); 2.95 (m, 2 H, CH$_2$ and isopropyl-H); 3.3 , 1 H, OH); 4.15 (m, 1 H, (OH)-CH); 5.1 , 1 H, OH); 6.7–7.35 (m, 14 H, aromatic-H).

Example 14

N-{2-[1-Ethyl-3-(4-fluorophenyl)-5-isopropyl-2-phenylpyrrol-4-yl]ethyl}-N-(3-carboxy-2-hydroxypropyl)hydroxylamine hydrochloride

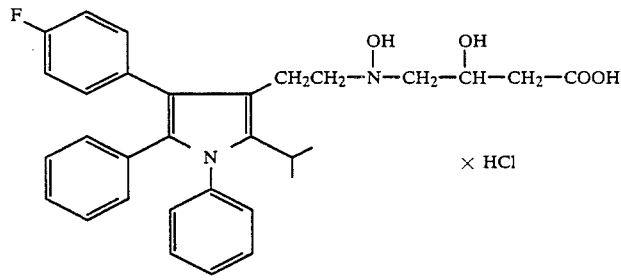

The compound is obtained from the compound of Example 13 using 1N hydrochloric acid which contains 20% dioxane analogously to Example 8. Colorless foam R$_f$=0.3 (chloroform/methanol 3:1).

Example 15

N-[2-(2,4-Dimethylphenyl)ethyl]-N-(3-carboxy-2-hydroxypropyl)hydroxylamine hydrochloride

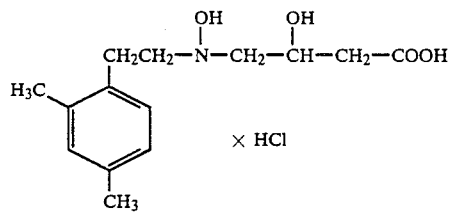

The compound is obtained from 2,4-dimethylbenzaldehyde analogously to Example 5–8.

Colorless foam.

$^1$H-NMR (d$_6$-DMSO+D$_2$O): δ=2.2 (m, 6 H, CH$_3$); 2.45 (m, overlapped by DMSO signal, CH$_2$); 2.95 (m, 2 H, CH$_2$); 3.35 (m, 4 H, CH$_2$); 4.3 (m, 1 H, HO—CH); 7.0 (m, 3 H, aromatic-H).

Example 16

N-[2-(2,4-Dimethylphenyl)ethyl]-N-(3-methoxycarbonyl-2-hydroxypropyl)hydroxylamine

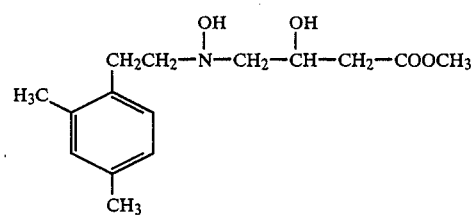

50 mg (0.19 mmol) of the compound from Example 15 is heated at reflux for 2 hours in 5 ml of methanol which contains 3 drops of concentrated hydrochloric acid. The mixture is concentrated to dryness, the residue is partitioned between ethyl acetate and saturated sodium hydrogen carbonate solution, the organic phase is dried over sodium sulphate and the solvent is removed in vacuo.

Yield: 40 mg (75%) of colorless oil.

MS: m/e=281 (15%, M+)); 233 (205, M-CH$_4$O); 162 (100%, M-C$_9$H$_{11}$).

Example 18

N-[2-(2,4-Dichlorophenyl)ethyl]-N-(3-tertiary butoxycarbonyl-2-hydroxypropyl)hydroxylamine

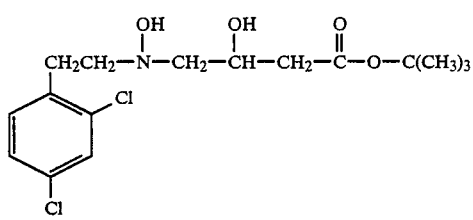

The compound is obtained from 2,4-dichlorobenzaldehyde analogously to Example 5-7.

Colorless oil.

$^1$H-NMR (CDCl$_3$): δ=1.45 (s, 9 H, C(CH$_3$)$_3$); 2.4 (d, 2 H, CH$_2$); 2.5 (d, 2 H, CH$_2$); 3.0 (m, 4 H, CH$_2$); 4.3 (m, 1 H, HO-CH); 5.9 (b, 1 H, OH); 7.15-7.3 (m, 3 H, aromatic-H).

Example 18

N-[2-(2,4-Dichlorophenyl)ethyl]-N-(3-carboxy-2-hydroxypropyl)hydroxylamine hydrochloride

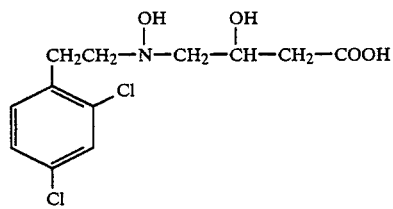

The compound is obtained from the compound of Example 17 analogously to Example 8.

Colorless foam.

Elemental analysis: Calc.: C 41.8 H 4.7 Cl 30.9 N 4.1.
Found: C 41.4 H 4.8 Cl 30.0 N 4.0.

Example 19

N-[2-(4'-Fluoro-3,5-dimethyl-1,1'-biphen-2-yl)ethyl]-N-(3-tertiary butoxycarbonyl-2-hydroxypropyl)hydroxylamine

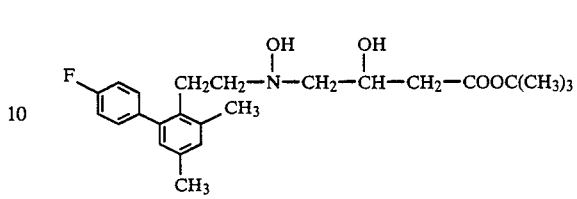

The compound is obtained from 4'-fluoro-3,5dimethyl-1,1'-biphenyl-2-carboxaldehyde (G. E. Stokker et al., J. Med. Chem. 29, 170 (1986)) analogously to Example 5-7.

$^1$H-NMR (CDCl$_3$): δ=1.45 (s, 9 H, C(CH$_3$)$_3$); 2.25-2.4 (m, 8 H, CH$_3$ and CH$_2$); 2.55 (m, 2 H, CH$_2$); 2.65 (m, 2 H, CH$_2$); 2.8 (m, 2 H, CH$_2$); 3.6 (b, 1 H, OH); 4.15 (m, 1 H, HO—CH); 4.9 (b, 1 H, OH); 6.8-7.3 (m, 6 H, aromatic-H).

Example 20

N-[2-(4'-Fluoro-3,5-dimethyl-1,1'-biphen-2-yl)ethyl]-N-(3-carboxy-2-hydroxypropyl) hydroxylamine hydrochloride

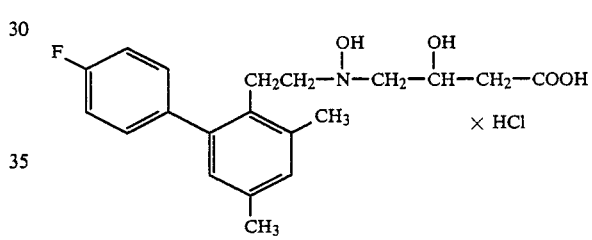

The compound is obtained from Example 19 analogously to Example 8. Colorless oil)

R$_f$=0.38 (chloroform/methanol 4:1)

Example 21

Ethyl 2-(4-fluoro-3-phenoxy-benzylidene)-4-methyl-3-oxopentanoate

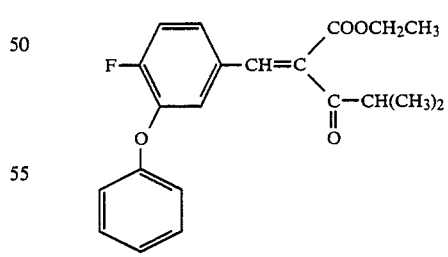

2.8 ml (29 mmol of piperidine and 1.7 ml (29 mmol) of acetic acid are added to a solution of 79 g (0.5 mol) of ethyl 4-methyl-3-oxo-pentanecarboxylate (prepared from methyl isopropyl ketone analogously to the process of S. B. Soloway and F. B. La Forge, J. Am. Chem. Soc. 69, 2677 (1947)) and 108 g (0.5 mol) of 4-fluoro-3-phenoxy-benzaldehyde in 300 ml of isopropanol and stirred overnight at RT. The mixture is then concentrated, the residue is taken up in 500 ml of ether, washed twice with water and once with saturated sodium chloride solution, dried over sodium sulphate and the solvent removed. The residue is distilled under high vacuum until the last fraction passes over at 185° C. and 0.3 mbar. All distillates (44 g) are discarded. The distillation residue contains the product: brownish oil (144.7 g, 81%), which is reacted further without purification.

R$_f$=0.25 (petroleum ether/ethyl acetate 10:1).

Example 22

3-Ethoxycarbonyl-2-(4-fluoro-3-phenoxy-phenyl)-5-methyl-1-phenylhexane-1,4-dione

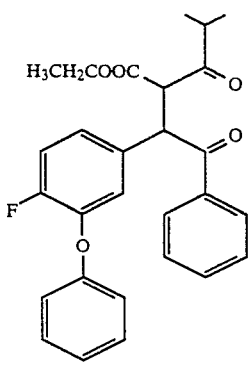

142.4 g (0.4 mol) of Example 21 are heated at reflux overnight with 42.4 g (0.4 mol) of benzaldehyde, 10.8 g (0.04 mol) of 3-benzyl-5-(2-hydroxyethyl)-4-methylthiazolium chloride and 33 ml of triethylamine in 270 ml of ethanol. The solvent is removed in vacuo, and the residue is dissolved in chloroform, washed twice with 1N sulphuric acid, water and saturated bicarbonate solution and dried over sodium sulphate. After concentrating to dryness, 185.2 g of yellowish oil remain. The crude product is sufficiently pure for further processing.

R$_f$=0.17 (petroleum ether/ethyl acetate 10:1).

Example 23

3-Ethoxycarbonyl-4-(4-fluoro-3-phenoxyphenyl)-2-isopropyl-5-phenylfuran

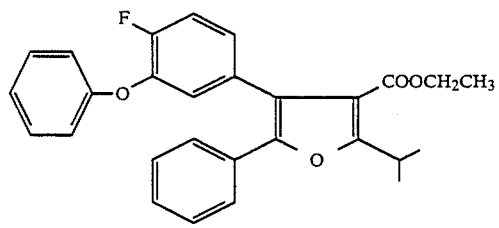

185 g (0.4 mmol) of the compound from Example 22 are boiled in a water separator for 2.5 hours with 15.2 g (0.05 mol) of p-toluenesulphonic acid hydrate in 2 l of toluene. 7 ml of water separates from the mixture, After cooling, the mixture is washed twice with saturated bicarbonate solution and once with sodium chloride solution, dried over sodium sulphate and concentrated to dryness. The residue is recrystallized from ethanol.

Yield: 57.9 g (33%) of colourless crystals.
m.p.: 99° C.

$^1$H-NMR (CDCl$_3$): δ=1.1 (t, 3H, 0—CH$_2$—CH$_3$); 1.35 (d, 6 H, isopropyl-CH$_3$); 3.8 (septet, 1 H, isopropyl-H); 4.15 (q, 2 H, 013 CH$_2$—CH$_3$); 6.1–7.35 (m, 13 H, aromatic-H).

Example 24

4-(4-Fluoro-3-phenoxyphenyl)-3-hydroxymethyl-2-isopropyl-5-phenylfuran

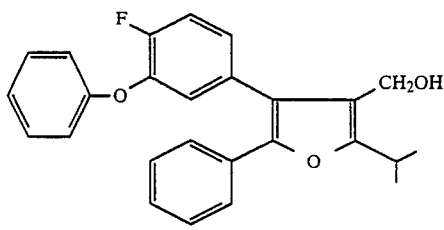

70 ml (84 mmol) of a 1.2M diisobutylaluminum hydride solution in toluene are slowly added dropwise at −78° C. under an argon atmosphere to a solution of 31 g (70 mmol) of the compound from Example 23 in 350 ml of anhydrous toluene in such a way that the temperature does not exceed −65° C. After stirring for 1 hour at −70° C., a further 58 mil (70 mmol) of DIBAH solution are added and the mixture is stirred for 1 more hour. 240 ml of 1N hydrochloric acid are then added dropwise at about −30° C. and finally 400 ml of water and 200 ml of ethyl acetate are added, as a result of which the mixture warms to room temperature. The aqueous phase is extracted 3 times with 250 ml of ethyl acetate, and the washed organic phases are washed with 400 ml of water and 400 ml of saturated sodium chloride solution and dried over sodium sulphate. The solvent is removed and the residue is dried under high vacuum.

Yield: 27.2 g (97%).
Colorless crystals
m.p.: 157° C.

Example 25

4-(4-Fluoro-3-phenoxyphenyl)-3-formyl-2-isopropyl-5-phenylfuran

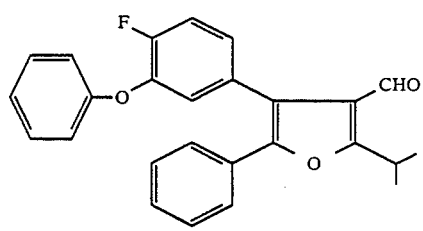

A solution of 13.8 ml (97 mmol) of trifluoroacetic anhydride in 90 ml of dichloromethane is added dropwise at −70° C. to −65° C. to 9.2 ml (130 mmol) of dimethyl sulphoxide in 70 ml of anhydrous dichloromethane and the mixture is stirred at this temperature for 10 minutes. 26.1 g (665 mmol) of the compound from Example 24, dissolved in 500 ml of dichloromethane, are then added dropwise and the mixture is stirred for 1 more hour at −65° C. 26.9 ml (195 mmol) of triethylamine are now added and the mixture is held at the same temperature for a further 10 minutes. After warming to RT, the mixture is washed with saturated bicarbonate solution and sodium chloride solution and dried over sodium sulphate, and the solvent is removed in vacuo. After boiling the residue with ethanol, 17.6 g (68%) of colorless solid remain of m.p.: 137° C. By cooling the ethanolic solution, a further 5.6 g (21%) are produced of m.p.:138° C.

¹H-NMR (CDCl₃): δ=1.4 (d, 6H, isopropyl-CH₃); 3.7 (septet, 1 H, isopropyl-H); 6.9–7.4 (m, 14 H, aromatic-H); 9.8 (s, 1 H, CHO).

Example 26

N-{2-[4-(4-fluoro-3-phenoxyphenyl)-2-isopropyl-5-phenylfuran-3-yl]ethyl}-N-(3-tertiary butoxycarbonyl-2-hydroxypropyl)hydroxylamine Solid colorless foam.

¹H-NMR (D₆-DMSO): δ=1.3 (d, 6 H, isopropyl-CH₃); 2.4 (m, overlapped by DMSO signal, CH₂); 2.8 (m, 2 H, CH₂); 3.0–3.3 (b, overlapped by H₂O signal, CH₂); 4.25 (b, 1 H, HOCH); 5.4 (very b, 1 H, OH); 6.9–7.6 (m, 14 H, aromatic-H).

Example 28

N-{2-[4-(4-Fluorophenyl)-2-isopropyl-5-phenylthiophen-3-yl]ethyl}-N-(3-tert.-butoxycarbonyl-2-hydroxypropyl)hydroxylamine

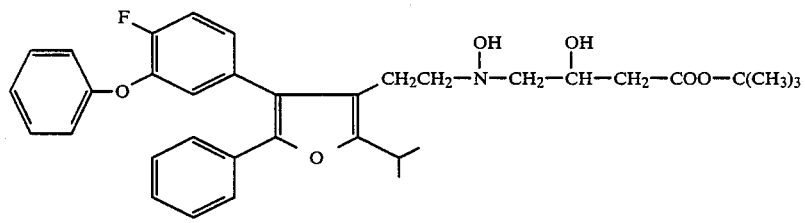

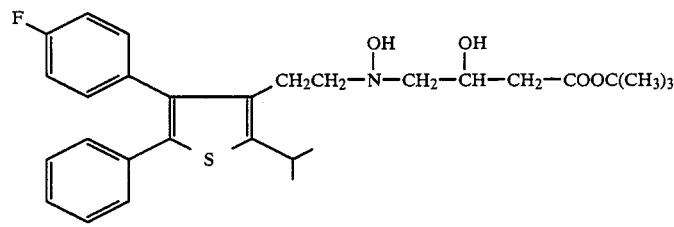

The compound is obtained from the compound of Example 25 analogously to Example 5–7.

Colorless foam.

¹H-NMR (CDCl₃): δ=1.4 (d, 6H, isopropyl-CH₃); 1.45 (s, 9 H, tert.butyl-CH₃); 2.4 (d, 2 H, CH₂); 2.6 (m, 6 H, CH₂); 3.1 (m, 1 H, isopropyl-H); 3.4 (b, 1 H, OH); 4.2 (1 H, HO—CH); 5.2 (b, 1 H, OH); 6.9–7.4 (m, 14 H, aromatic-H).

Example 27

N-{2-[4-(4-Fluoro-3-phenoxyphenyl)-2-isopropyl-5-phenylfuran-3-yl]ethyl}-N-(3-carboxy-2-hydroxypropyl)hydroxylamine hydrochloride The compound is obtained from 4-(4-fluorophenyl)-3-formyl-2-isopropyl-5-phenylthiophene analogously to Example 5–7.

Colorless foam.

¹H-NMR (CDCl₃): δ=1.38 (d, 6 H, isopropyl-CH₃); 1.45 (s, 9 H, tert.butyl); 2.35 (d, 2 H, CH₂); 2.5–2.65 (m, 4 H); 2.75 (m, 2 H, CH₂); 3.35 (m, 2 H, isopropyl-H +OH); 4.15 (m, 1 H, HO-CH); 5.1 (b, 1 H, OH); 7.0–7.2 (m, 9 H, aromatic-H).

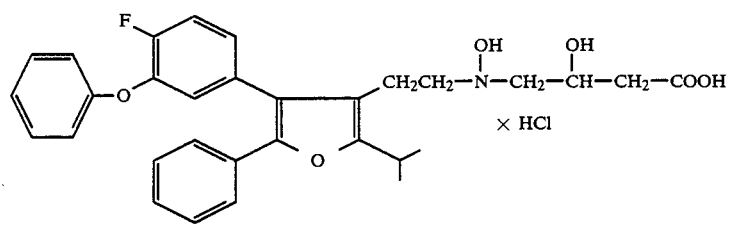

The compound is obtained from the compound of Example 26 analogously to Example 8.

Example 29

N-{2-[4-(4-Fluorophenyl)-2-isopropyl-5-phenylthiophen-3-yl]ethyl}-N-(3-carboxy-2-hydroxypropyl)hydroxylamine hydrobromide

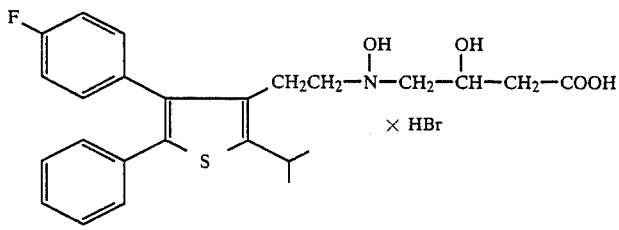

0.7 g (1.4 mmol) of the compound from Example 28 is heated at reflux for 1 hour in 25 ml of 1N hydrobromic acid and 5 ml of dioxane. The solvent is removed in vacuo and the residue is recrystallized from ether.

Yield: 0.64 g (84%) of colorless crystals.

m.p.: 135°–140° C. (dec.).

$R_f = 0.4$ (chloroform/methanol 3:1).

$^1$H-NMR (CD$_3$OD): $\delta = 1.4$ (d, 6 H, isopropyl-CH$_3$); 2.5 (d, 2 H, CH$_2$); 3.0 (m, 2 H, CH$_2$); 3.15–3.5 (m, overlapped by CD$_3$OD signal); 4.3 (b, 1 H); 7.1–7.3 (m, 9 H, aromatic-H).

Example 30

1-(4-Fluorophenyl)-4-methyl-2-phenyl-penten-3-one

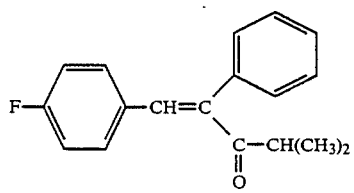

31 g (0.25 mol) of 4-fluorobenzaldehyde, 40.6 g (0.25 mol) of benzyl isopropyl ketone, 2.5 ml of piperidine and 1.75 ml of glacial acetic acid are boiled in a water separator for 20 hours in 200 ml of toluene. After removing the solvent, the residue is distilled through a 20 cm Vigreux column.

Yield: 56.8 g (85%) of yellowish oil.

b.p.: 140° C. (0.2 mbar), which completely crystallizes in the refrigerator (m.p.: 47° C.).

Example 31

2-(4-Fluorophenyl)-5-methyl-1-nitro-3-phenylhexan-4-one

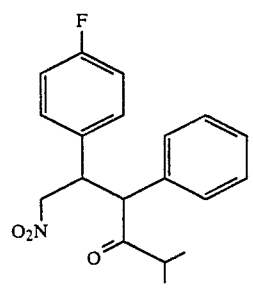

A solution of 31 g (0.2 mol) of DBU in 100 ml of acetonitrile is added dropwise at room temperature to a solution of 53 g (0.2 mol) of Example 30 and 29 g (0.47 mol) of nitromethane in 200 ml of acetonitrile and the mixture is stirred overnight at room temperature. The solvent is evaporated, the residue is partitioned between 500 ml of 1N hydrochloric acid and 500 ml of dichloromethane, and the organic phase is washed with saturated sodium chloride solution and sodium hydrogen carbonate solution and dried over sodium sulphate. The residue is recrystallized from ether.

Yield: 26.4 g (40%) of colorless crystals.

m.p. 178° C.

$^1$H-NMR (CDCl$_3$): $\delta = 0.68 + 0.77$ (two d, 6 H, isopropyl-CH$_3$); 2.4 (m, 1 H, isopropyl-H); 4.15–4.5 (m, 4H); 7.0 (t, 2 H, F-C-CH); 7.25–7.45 (m, 7 H, aromatic-H).

Example 32

4-Fluorophenyl-1,2-diisopropyl-3-phenylpyrrole

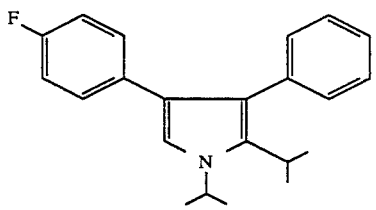

A solution of 26.5 g (80 mmol) of Example 31 in 200 ml of ethanol and 50 ml (0.1 mol) of 2N sodium hydroxide solution is added dropwise at 0° C. to a solution of 22.5 g (0.2 mol) of sulphuric acid in 100 ml of ethanol and 50 ml of water and then stirred for 1 hour at room temperature. The mixture is filtered off from a little precipitate, the concentrated filtrate is partitioned between chloroform and water, and the organic phase is washed with 1N hydrochloric acid and saturated sodium hydrogen carbonate solution and dried over sodium sulphate. After removing the solvent, 24 g of a dark oil (crude product of 2-fluorophenyl-5-methyl-4-oxo-3-phenylhexanal) remain. $R_f = 0.2$ (petroleum ether/ethyl acetate 2:1).

The above oil is dissolved in 400 ml of toluene together with 29 g (0.5 mol) of isopropylamine. 15.3 g (80 mmol) of titanium tetrachloride in 50 ml of toluene are added dropwise to this at 0° C. and the mixture is stirred for 6 hours at room temperature. The mixture is filtered through kieselguhr with suction, and washed well with toluene, and the filtrate is extracted twice with 6N hydrochloric acid, washed with saturated bicarbonate solution and dried over sodium sulphate. After concentrating, 26 g of a dark oil remain which is filtered through a short silica gel column (petroleum ether/dichloromethane 2:1).

From the eluate, 3.25 g (13%) of colorless crystals are obtained.

m.p.: 150° C.

$^1$H-NMR (CDCl$_3$): δ=1.25 (d, 6 H, C-isopropyl-CH$_3$); 1.5 (d, 6 H, N-isopropyl-CH$_3$); 3.2 (septet, 1 H, C-isopropyl-H); 4.55 (septet 1 H N-isopropyl-H); 6.8 (s, 1 H, 5-H); 6.8–7.3 (m, 9 H, aromatic-H).

Example 33

3-(4-Fluorophenyl)-2-formyl-1,5-diisopropyl-4-phenyl-pyrrole

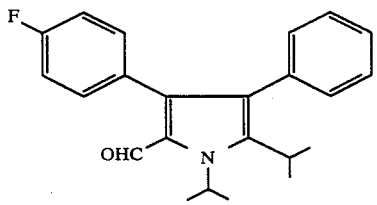

0.92 g (10 mmol) of phosphorus oxychloride is added dropwise at room temperature to a solution of 3.25 g (10 mmol) of Example 32 in 50 ml of dimethylformamide, and the mixture is stirred at room temperature for 1 hour and at 40° C. for 2 hours and then poured into 40 ml of icecold 1N sodium hydroxide solution (pH ~ 9). The mixture is extracted three times using ethyl acetate, and the organic phase is washed with water and dried over sodium sulphate. After evaporating the solvent, a solid residue (3.5 g) remains which is recrystallized from methylene chloride/petroleum ether.

Yield: 3.0 g (85%) of slightly colored crystals.
m.p.: 160° C.

Example 34

1-[3-(4-Fluorophenyl)-1,5-diisopropyl-4-phenyl-pyrrol-2yl]-2-nitroethene

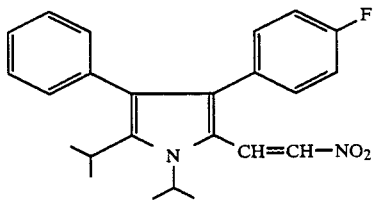

1.1 g (3.15 mmol) of Example 33 and 32 mg (0.53 mmol) of 1,2- diaminoethane are stirred at 7520 C. for 17 hours in 12 of nitromethane. The mixture is taken up in dichloromethane, washed twice with water, dried over sodium sulphate and the residue is recrystallized from ether/petroleum ether.

Yield: 1.09 g (88%) of orange crystals.
m.p.: 238° C.

$^1$H-NMR (CDCl$_3$): =1.3 (d, 6 H, C-isopropyl-CH$_3$); 1.75 (d, 6 H, N-isopropyl-H); 3.28 (m, 1 H, C-isopropyl-CH$_3$); 4.85 (m, 1 H, N-isopropyl-H); 6.6 (db, 1 H, olefinic-H); 6.9–7.25 (m, 9 H, aromatic-H); 8.85 (db, 1 H, olefinic-H).

Example 35

N-{2-[3-(4-Fluorophenyl)-1,5-diisopropyl-4-phenyl-pyrrol-2-yl]ethyl}-N-(3-tert.-butoxycarbonyl-2-hydroxypropyl)hydroxylamine

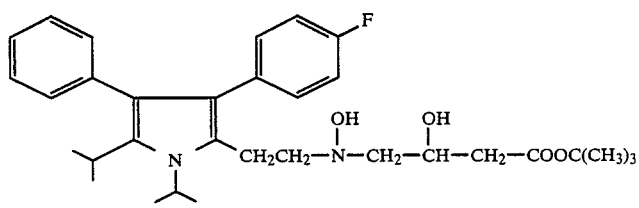

The compound is obtained from the compound of Example 34 analogously to Example 6 and 7.

Colorless foam.

$^1$H-NMR (CDCl$_3$): δ=1.05–1.3 (b, 6 H, isopropyl-CH$_3$); 1.45 (s, 9 H, tert.-butyl); 1.62 (d, 6 H, isopropyl-CH$_3$); 2.35 (b, 2 H, CH$_2$); 2.45–2.75 (b, 4 H, CH$_2$); 2.85 (b, 2 H, CH$_2$); 3.15 (b, 1 H, OH); 3.3 ) (m, 1 H, C-isopropyl-H); 4.15 (b, 1 H, HO-CH); ); 4.6 (b, 1 H, N-isopropyl-H); 5.2 (b, 1 H, OH); 6.75–7.2 (mb, 9 H, aromatic-H).

Example 36

N-{2-[3-(4-Fluorophenyl)-1,5-diisopropyl-4-phenylpyrrol-2-yl]ethyl}-N-(3-carboxy-2-hydroxy-propyl)hydroxylamine hydrobromide

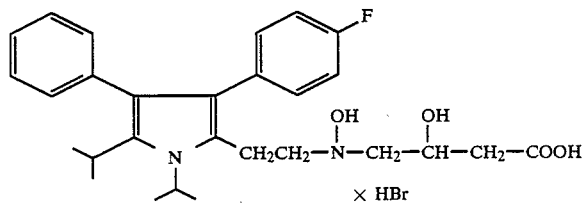

From the compound of Example 35 analogously to Example 29. The crude product is chromatographed on 25 times the amount of silica gel (230–400 mesh) using 200 ml each of chloroform and methanol 10:1 and 5:1. Yield: 56% of colorless crystals (from ether) which decompose from 170° C.

R$_f$=0.45 (chloroform/methanol 3:1).

$^1$H-NMR (CD$_3$OD): δ=1.05–1.3 (b, 6 H, isopropyl-CH$_3$); 1.6 (d, 6H, isopropyl-CH$_3$); 2.3–3.2 (b, 8 H); 4.2 (b, 1 H, HO—CH); 4.7 (b, 1 H, N-isopropyl); 6.7–7.2 (b, 9 H, aromatic-H).

USE EXAMPLE

Example 37

The determination of enzyme activity was carried out by a modification of the procedure of G. C. Ness et al., Archives of Biochemistry and Biophysics 197, 493–499 (1979). Male Rico rats (body weight 300–400 g) were treated for 11 days with altromin powder feed to which 40 g of cholestyramine/kg of feed had been added. After decapitation, the liver was removed from the animals and placed on ice. The livers were comminuted and homogenized 3 times in 3 volumes of 0.1M saccharose, 0.05M KCl, 0.04M $K_xH_y$ phosphate (mixture of $K_2HPO_4$ and $KH_2PO_4$ having pH of 7.2), 0.03M ethylenediaminetetraacetic acid, 0.002M dithiothreitol (SPE) buffer (saccharose/phosphate/ ethylenediaminetetraacetate buffer) pH 7.2 in a homogenizer. The homogenate was then centrifuged for 15 minutes and the sediment discarded. The supernatant was sedimented for 75 minutes. The pellet is taken up in ¼ volumes of SPE buffer, homogenized once more and then centrifuged again for 60 minutes. The pellet was taken up in 5 times its volume of SPE buffer, homogenized and frozen and stored at $-78°$ C. (=enzyme solution).

The test compounds (or mevinolin as the reference substance) were dissolved in dimethylformamide with the addition of 5% by volume of 1N NaOH for testing and were employed in the enzyme test in various concentrations using 10 μl. The test was started after pre-incubation of the compounds with the enzyme at 37° C. for 20 minutes. The test batch was 0.380 ml and contained 4 μmol of glucose-6-phosphate, 1.1 mg of bovine serum albumin, 2.1 mol of dithiothreitol, 0.35 μmol of NADP, 1 unit of glucose-6-phosphate dehydrogenase, 35 μmol of $K_xH_y$ phosphate PH 7.2, 20 μl of enzyme preparation and 56 nmol of 3 hydroxy-3-methyl-glutaryl coenzyme A (glutaryl-3-$^{14}$C) 100,000 dpm.

The mixture was incubated at 37° C. for 60 minutes and the reaction was stopped by the addition of 300 μl of 0.24M HCl. After a post-incubation of 60 minutes at 37° C., the batch was centrifuged and 600 μl of the supernatant was applied to a 0.7×4 cm column filled with 5-chloride anion exchanger having a particle size of 100–200 mesh (anion exchanger). The column was washed with 2 ml of distilled water and 3 ml of a scintillation fluid was added to the eluent plus washing water and counted in a scintillation counter. $IC_{50}$ values were determined by intrapolation by plotting the percentage inhibition against the concentration of the compound in the test. For the determination of the relative inhibitory potency, the $IC_{50}$ value of the reference substance mevinolin was set at 100 and compared with the simultaneously determined $IC_{50}$ value of the test compound.

It is understood that the specification and examples are illustrative but not limitative of the present invention and that other embodiments within the spirit and scope of the invention will suggest themselves to those skilled in the art.

We claim:

1. A substituted hydroxylamine of the formula (I)

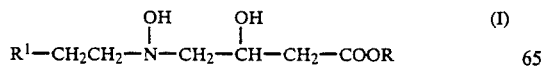

in which
R stands for hydrogen,
stands for ester radical, or
stands for a cation, and
$R^1$ stands for a group of the formula

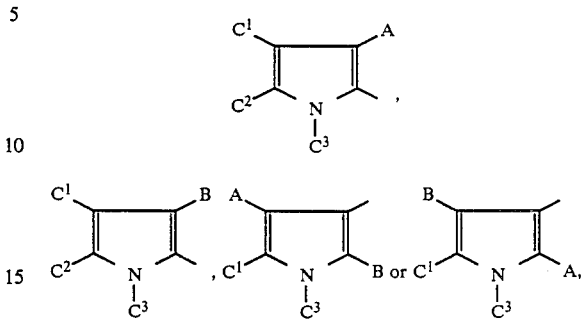

A denotes thienyl, furyl, thiazolyl, isothiazolyl, oxazolyl, isoxazolyl, pyridyl, pyrimidyl, pyrazinyl, pyridazinyl, indolyl, isoindolyl, quinolyl, isoquinolyl, phthalazinyl, quinoxalinyl, quinazolinyl, cinnolinyl, benzothiazolyl, benzoxazolyl or benzimidazolyl, each of which can be monosubstitutred or disubstituted by identical or different flourine, chlorine, bromine, lower alkyl, lower akloxy, phenyl, phenoxy, trifluoromethyl, trifluoromethoxy or lower alkoxycarbonyl substituents, or denotes phenyl or naphthyl, each of which can be monosubstituted to tetrasubstituted by lower alkyl, lower alkoxy, lower alkylthio, lower alkylsulphonyl, phenyl, phenyloxy, phenylthio, phenylsulphonyl, benzyl, benzyloxy, benzylthio, benzylsulphonyl, phenethyl, phenethoxy, phenethylthio, phenethylsulphonyl, fluorine, chlorine, bromine, cyano, trifluoromethyl, trifluoromethoxy, trifluoromethylthio, lower alkoxycarbonyl or by a group of the formula $-NR^5R^6$, the substituents being identical or different, wherein
$R^5$, $R^6$ are identical or different and denote alkyl, aryl, aralkyl, acyl, alkylsulphonyl or arylsulphonyl,
B denotes cycloalkyl, or
denotes alkyl which can be substituted by halogen, cyano, alkoxy, alkylthio, alkylsulphonyl, trifluoromethyl, trifluoromethoxy, alkoxycarbonyl, acyl or by a group of the formula $-NR^5R^6$,
or by carbamoyl, dialkylcarbamoyl, sulphamoyl, dialkylsulphamoyl, heteroaryl, aryl, aryloxy, arylthio, arylsulphonyl, aralkoxy, aralkylthio or aralkylsulphonyl, where the heteroaryl and aryl radicals can be monosubstituted, disubstituted or trisubstituted by identical or different halogen, cyano, trifluoromethyl, trifluoromethoxy, alkyl, alkoxy, alkylthio or alkylsulphonyl substituents, and
$C^1$, $C^2$, $C^3$ are identical or different and
denote hydrogen, or
denote cycloalkyl, or
denote alkyl which can be substituted by halogen, cyano, alkoxy, alkylthio, alkylsulphonyl, trifluoromethyl, trifluoromethoxy, trifluoromethylthio, trifluoromethylsulphonyl, alkoxycarbonyl, acyl or by a group of the formula $-NR^5R^6$,
or by carbamoyl, dialkylcarbamoyl, sulphamoyl, dialkylsulphamoyl,
or by pyridyl, pyrimidyl, pyrazinyl, pyridazinyl, quinolyl, isoquinolyl, pyrryl, indolyl, thienyl, furyl, imidazolyl, oxazolyl, thiazolyl, phenyl, phenoxy, phenylthio, phenylsulphonyl, benzyloxy, benzylthio, benzyluslphonyl, phenethoxy, phenethylthio or phenethylsulphonyl, optionally monosubstituted or disubstituted by identical or different fluorine, chlorine, bromine, lower alkyl, lower alkoxy, trifluoromethyl, or trifluoromethoxy substituents, or denotes phenyl or naphthyl, each of which can be monosubstituted to tetrasubstituted by lower alkyl, lower alkoxy, lower alkylthio, lower alkylsulphonyl, phenyl, phenyloxy, phenylthio, phenylsulphonyl, benzyl, benzyloxy, benzylthio, benzylsulphonyl, phenethyl, phenethoxy, phenethylthio, phenethylsulphonyl, fluorine, chlorine, bromine, cyano, trifluoromethyl, trifluoromethoxy, trifluoromethylthio, lower alkoxycarbonyl or by a group of the formula $-NR^5R^6$, the substituents being identical or different.

2. A substituted hydroxylamine according to claim 1, in which

R stands for hydrogen or stands for a physiologically tolerable ester radical, or stands for a physiologically tolerable cation, $R^5$ and $R^6$ are identical or different and denote lower alkyl, phenyl, benzyl, acetyl, benzoyl, phenylsulphonyl or lower alkylsulphonyl, B denotes cyclopropyl, cyclopentyl or cyclohexyl, or
denotes lower alkyl which can be substituted by fluorine, chlorine, bromine, cyano, lower alkoxy, lower alkylthio, lower alkylsulphonyl, trifluoromethyl, trifluoromethoxyl, trifluoromethylsulphonyl, lower alkoxycarbonyl, benzoyl, lower alkylcarbonyl, by a group of the formula $-NR^5R^6$, or by pyridyl, pyrimidyl, pyrazinyl, pyridazinyl, quinolyl, isoquinolyl, pyrryl, indolyl, thienyl, furyl, imidazolyl, oxazolyl, thiazolyl, phenyl, phenoxy, phenylthio, pheylsulphonyl, benzyloxy, benzylthio, benzylsulphonyl, phenethoxy, phenethylthio or phenethylsulphonyl, where the heteroaryl and aryl radicals mentioned can be monosubstituted or disubstituted by identical or different fluorine, chlorine, bromine, lower alkyl, lower alkoxy, trifluoromethyl, or trifluoromethyoxy substituents, $C^1$, $C^2 C^3$ are identical or different and denote hydrogen, or denote cyclopropyl, cyclopentyl or cyclohexyl, or denote lower alkyl which can be substituted by fluorine, chlorine, bromine, cyano, lower alkoxy, lower alkylthio, lower alkylsulphonyl, trifluoromethyl, trifluoromethoxy, trifluoromethylsulphonyl, lower alkoxycarbonyl, benzoyl, lower alkylcarbonyl, by a group of the formula $-NR^5R^6$, or by pyridyl, pyrimidyl, pyrazinyl, pyridazinyl, quinolyl, isoquinolyl, pyrrolyl, indolyl thienyl, furyl, imidazolyl, oxazolyl, thiazolyl, phenyl, phenoxy, phenylthio, phenylsulphonyl, benzyloxy, benzylthio, benzylsulphonyl, phenethoxy, phenethylthio or phenethylsulphonyl, where the heteroaryl and aryl radicals mentioned can be monosubstituted or disubstituted by identical or different fluorine, chlorine, bromine, lower alkyl, lower alkoxy, trifluoromethyl, or trifluoromethyoxy substituents, or denotes phenyl or naphthyl, each of which can be monosubstituted to tetrasubstituted by lower alkyl, lower alkoxy, lower alkylthio, lower alkylsulphonyl, phenyl, phenyloxy, phenylthio, phenylsulphonyl, benzyl, benzyloxy, benzylthio, benzylsulphonyl, phenethyl, phenylethoxy, phenethylthio, phenethylsulphonyl, fluorine, chlorine, bromine, cyano, trifluoromethyl, trifluoromethoxy, trifluoromethylthio, lower alkoxycarbonyl or by a group of the formula $-NR^5R^6$, the substituents being identical or different.

3. A substituted hydroxylamine according to claim 1, in which

R stands for hydrogen, methyl, ethyl, propyl, isopropyl, butyl, isobutyl, tert.-butyl or benzyl, or stands for a magnesium or ammonium cation, A denotes pyridyl, pyrimidyl, quinolyl or isoquinolyl, each of which can be substituted by fluorine, chlorine, methyl, methoxy or trifluoromethyl, or denotes phenyl which can be monosubstituted, disubstituted or trisubstituted by identical or different methyl, ethyl, propyl, isopropyl, butyl, isobutyl, tert.-butyl, methoxy, ethoxy, propoxy, isopropoxy, butoxy, isobutoxy, tert.-butoxy, methylthio, ethylthio, propylthio, isopropylthio, methylsulphonyl, ethylsulphonyl, propylsulohonyl, isopropylsulphonyl, phenyl, phenoxy, benzyl, benzyloxy, fluorine, chlorine, bromine, cyano, trifluoromethyl, trifluoromethoxy, methoxycarbonyl, ethoxycarbonyl, propoxycarbonyl, isopropoxycarbonyl, butoxycarbonyl, isobutoxycarbonyl or tert.-butoxycarbonyl substituents, B denotes cyclopropyl, cyclopentyl or cyclohexyl, or
denotes methyl, ethyl, propyl, isopropyl, butyl, sec.-butyl or tert.-butyl, each of which can be substituted by fluorine, chlorine, bromine, cyano, methoxy, ethoxy, propoxy, isopropoxy, butoxy, sec.-butoxy, tert.-butoxy, methylthio, ethylthio, propylthio, isopropylthio, methylsulphonyl, ethylsulphonyl, propylsulphonyl, isopropylsulphonyl, trifluoromethyl, trifluoromethoxy, methoxycarbonyl, ethoxycarbonyl, butoxycarbonyl, isobutoxycarbonyl, tert.-butoxycarbonyl, benzoyl, acetyl, pyridyl, pyrimidyl, thienyl, furyl, phenyl, phenoxy, phenylthio, phenylsulphonyl, benzyloxy, benzylthio or benzylsulphonyl, $C^1$, $C^2$, $C_3$ are identical or different and denote hydrogen, cyclopropyl, cyclopentyl or cyclohexyl, or denote methyl, ethyl, propyl, isopropyl, butyl, isobutyl, tert.-butyl, pentyl, isopentyl, hexyl or isohexyl, each of which can be substituted by fluorine, chlorine, bromine, cyano, methoxy, ethoxy, propoxy, isopropoxy, butoxy, isobutoxy, tert.-butoxy, methylthio, ethylthio, propylthio, isopropylthio, butylthio, isobutylthio, tert.-butylthio, methylsulphonyl, ethylsulphonyl, propylsulphonyl, isopropylsulphonyl, butylsulphonyl, isobutylsulphonyl, tert.-butylsulphonyl, trifluoromethyl, trifluoromethoxy, methoxycarbonyl, ethoxycarbonyl, propoxycarbonyl, isopropoxycarbonyl, butoxycarbonyl, isobutoxycarbonyl, tert.-butoxycarbonyl, benzoyl, acetyl, ethylcarbonyl, or by a group $-NR^5R^6$, where $R^5$ and $R^6$ are identical or different and denote methyl, ethyl, propyl, isopropyl, butyl, isobutyl, tert.-butyl, phenyl, benzyl, acetyl, methylsulphonyl, ethylsulphonyl, propylsulphonyl, isopropylsulphonyl or phenylsulphonyl, or by pyridyl, pyrimidyl, pyrazinyl, pyridazinyl, quinolyl, isoquinolyl, thienyl, furyl, phenyl, phenoxy, phenylthio, phenylsulphonyl, benzyloxy, benzylthio or benzylsulphonyl, where the heteroaryl and aryl radicals can be substituted by fluorine, chlorine, methyl, ethyl, propyl, isopropyl, isobutyl, tert.-butyl, methoxy, ethoxy, propoxy, isopropoxy, butoxy, isobutoxy, tert.-butoxy, trifluoromethyl or trifluoromethoxy, or denotes thienyl, furyl, pyridyl, pyrimidyl, pyrazinyl, pyridazinyl, oxazolyl, isooxazolyl, imidazolyl, pyrazolyl, thiazolyl, isothiazolyl, quinolyl, isoquinolyl, benzoxazolyl, benzimidazolyl or benzthiazolyl, where the radicals can be substituted by fluorine, chlorine, methyl, ethyl, propyl, isopropyl, butyl, isobutyl, tert.-butyl, methoxy, ethoxy, propoxy, isopropoxy, butoxy, isobutoxy, tert.butoxy, phenyl, phenoxy, trifluoromethyl, trifluoromethoxy, methoxycarbonyl, ethoxycarbonyl, isopropoxycarbonyl, propoxycarbonyl, butoxycarbonyl, isobutoxycarbonyl or tert.-butoxycarbonyl, or denotes phenyl which can be monosubstituted, disubstituted or trisubstituted by methyl, ethyl, propyl, isopropyl, butyl, isobutyl, tert.-butyl, pentyl, isopentyl, hexyl, isohexyl, methoxy, ethoxy, propoxy, isopropoxy, butoxy, isobutoxy, tert.-butoxy, methylthio, ethylthio, propylthio, isopropylthio, butylthio, isobutylthio, tert.-butylthio, methylsulphonyl, ethylsulphonyl, propylsulphonyl, isopropylsulphonyl, butylsulphonyl, isobutylsulphonyl, tert.-butylsulphonyl, phenyl, phenoxy, phenylthio, phenylsulphonyl, benzyl, benzyloxy, benzylthio, benzylsulphonyl, fluorine, chlorine, bromine, cyano, trifluoromethyl, trifluoromethoxy, trifluoromethylthio, methoxycarbonyl, ethoxycarbonyl, propoxycarbonyl, isopropoxycarbonyl, butoxycarbonyl, isobutoxycarbonyl, tert.-butoxycarbonyl or by a group $-NR^5R^6$, the substituents being identical or different.

4. A composition for the treatment of hyperlipoproteinaemia, lipoproteinaemia or atherosclerosis which comprises an amount effective therefor of a compound or salt according to claim 1 and a diluent.

5. A method of treating hyperlipoproteinaemia, lipoproteinaemia or atherosclerosis in a patient afflicted therewith which comprises administering to such patient an amount effective therefor of a compound or salt according to claim 1.

* * * * *